(12) United States Patent
Yersin et al.

(10) Patent No.: US 9,024,026 B2
(45) Date of Patent: May 5, 2015

(54) COPPER (I) COMPLEXES FOR OPTOELECTRONIC DEVICES

(75) Inventors: Hartmut Yersin, Sinzing (DE); Rafal Czerwieniec, Obertraubling (DE); Uwe Monkowius, Linz (AT)

(73) Assignee: Cynora GmbH, Bruchsal (DE)

( * ) Notice: Subject to any disclaimer, the term of this patent is extended or adjusted under 35 U.S.C. 154(b) by 0 days.

(21) Appl. No.: 13/810,848

(22) PCT Filed: Jul. 20, 2011

(86) PCT No.: PCT/EP2011/062491
§ 371 (c)(1),
(2), (4) Date: Feb. 14, 2013

(87) PCT Pub. No.: WO2012/010650
PCT Pub. Date: Jan. 26, 2012

(65) Prior Publication Data
US 2013/0150581 A1 Jun. 13, 2013

(30) Foreign Application Priority Data

Jul. 20, 2010 (DE) .......................... 10 2010 031 831

(51) Int. Cl.
| | |
|---|---|
| *C09K 11/06* | (2006.01) |
| *C07D 471/04* | (2006.01) |
| *C07F 5/02* | (2006.01) |
| *C07F 9/50* | (2006.01) |
| *C07F 9/6561* | (2006.01) |
| *H01L 51/00* | (2006.01) |
| *H01L 51/50* | (2006.01) |

(52) U.S. Cl.
CPC .............. *C09K 11/06* (2013.01); *C07D 471/04* (2013.01); *C07F 5/027* (2013.01); *C07F 9/5027* (2013.01); *C07F 9/5045* (2013.01); *C07F 9/6561* (2013.01); *H01L 51/008* (2013.01); *H01L 51/009* (2013.01); *H01L 51/0091* (2013.01); *H01L 51/0072* (2013.01); *H01L 51/5012* (2013.01); *Y02E 10/549* (2013.01); *C09K 2211/1007* (2013.01); *C09K 2211/1011* (2013.01); *C09K 2211/1029* (2013.01); *C09K 2211/188* (2013.01)

(58) Field of Classification Search
None
See application file for complete search history.

(56) References Cited

U.S. PATENT DOCUMENTS

| 1,028,479 | A1 | 11/2011 | Stoessel et al. |
|---|---|---|---|
| 2010/0176386 | A1 | 7/2010 | Yersin et al. |
| 2011/0155954 | A1 | 6/2011 | Yersin et al. |

FOREIGN PATENT DOCUMENTS

| DE | 102007031261 A1 | 1/2009 |
|---|---|---|
| DE | 102008048336 A1 | 3/2010 |
| WO | WO-2010086089 A1 | 8/2010 |

OTHER PUBLICATIONS

European Patent Office International Search Report for International Application No. PCT/EP2011/062491 mailed Dec. 5, 2011 (6 pages).
Zhang, Qisheng et al., "Highly Efficient Green Phosphorescent Organic Light-Emitting Diodes Based on $Cu^I$ Complexes," Mar. 5, 2004 Adv. Mater., vol. 16, No. 5 (pp. 432-436).
Zhang, Qisheng et al., "Novel Heteroleptic $Cu^I$ Complexes with Tunable Emission Color for Efficient Phosphorescent Light-Emitting Diodes," Oct. 1, 2007, Adv. Funct. Mater., vol. 17, No. 15 (pp. 2983-2990).

*Primary Examiner* — Timothy R Rozof
(74) *Attorney, Agent, or Firm* — Harris Beach PLLC

(57) ABSTRACT

The invention relates to neutral mononuclear copper (I) complexes for emitting light and with a structure according to formula (A) in which: M represents: Cu(I); L∩L represents: a single, negatively charged, bidentate ligand; N∩N represents: a diimine ligand (substituted with R and FG), in particular a substituted 2,2'-bipyridine derivative (bpy) or a substituted 1,10-phenanthroline derivative (phen); R represents: at least one sterically demanding substituent for preventing the planarization of the complex in the excited state; FG=functional group, and represents: at least one second substituent for increasing solubility in organic solvents. The substituent can also be used for electron transport or alternatively for hole transport, said functional group being bound to the diimine ligands either directly or by means of suitable bridges; and the copper (I) complex: having a $\Delta E(S_1-T_1)$ value of less than 2500 $cm^{-1}$ between the lowest excited singlet state ($S_1$) and the triplet state ($T_1$) which lies below; having an emission lifespan of at most 20 μs; having an emission quantum yield of greater than 40%, and a solubility of at least 1 g/L in organic solvents, in particular polar organic hydrocarbons such as acetone, methyl ethyl ketone, benzene, toluene, chlorobenzene, dichlorobenzene, dichloromethane, chloroform, dichloroethane, tetrachloroethylene, alcohols, acetonitrile or water.

21 Claims, 8 Drawing Sheets

COPPER (I) COMPLEXES FOR OPTOELECTRONIC DEVICES

CROSS-REFERENCE TO RELATED APPLICATIONS

Figure 1:
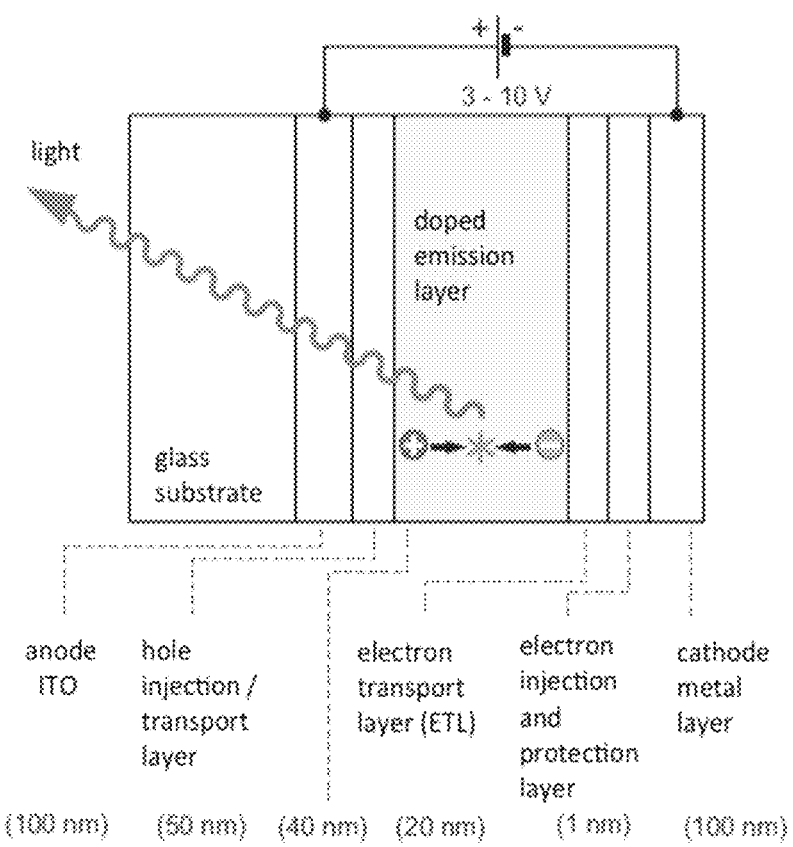

This application is a national stage application under 35 U.S.C. §371 of PCT Application No. PCT/EP2011/062491, filed Jul. 20, 2011, which claims priority to and the benefit of German Application No. DE 10 2010 031 831.0, filed Jul. 20, 2010, which is incorporated herein by reference in its entirety.

The present invention relates to the use of soluble copper(I) complexes (Cu(I)-complexes) as emitters in OLEDs (organic light-emitting diodes) and in other optoelectronic devices.

INTRODUCTION

A dramatic change is currently on the horizon in the field of visual display and illumination technology. It will be possible to manufacture flat displays or illuminated surfaces having a thickness of less than 0.5 mm. These are notable for many fascinating properties. For example, it will be possible to achieve illuminated surfaces in the form of wallpaper with very low energy consumption. It is also of particular interest that color visual display units will be producible with hitherto unachievable colorfastness, brightness and viewing angle independence, with low weight and with very low power consumption. It will be possible to configure the visual display units as micro-displays or large visual display units of several square meters in area in rigid form or flexibly, or else as transmission or reflection displays. In addition, it will be possible to use simple and cost-saving production processes such as screen printing or inkjet printing or vacuum sublimation. This will enable very inexpensive manufacture compared to conventional flat visual display units. This new technology is based on the principle of the OLEDs, the organic light-emitting diodes. Furthermore, through the use of specific organic materials (molecules), many new optoelectronic applications are on the horizon, for example in the field of organic solar cells, organic field-effect transistors, organic photodiodes, etc.

Particularly for the OLED sector, it is apparent that such devices are already now of economic significance, since mass production is expected shortly. Such OLEDs consist predominantly of organic layers, which can also be manufactured flexibly and inexpensively. OLED components can also be configured with large areas as illumination bodies, but also in small form as pixels for displays.

Compared to conventional technologies, for instance liquid-crystal displays (LCDs), plasma displays or cathode ray tubes (CRTs), OLEDs have numerous advantages, such as a low operating voltage of a few volts, a thin structure of only a few hundred nm, high-efficiency self-illuminating pixels, high contrast and good resolution, and the possibility of representing all colors. In addition, in an OLED, light is produced directly on application of electrical voltage, rather than merely being modulated.

A review of the function of OLEDs can be found, for example, in H. Yersin, Top. Curr. Chem. 2004, 241, 1 and H. Yersin, "Highly Efficient OLEDs with Phosphorescent Materials"; Wiley-VCH, Weinheim, Germany, 2008.

Since the first reports regarding OLEDS (see, for example, Tang et al., Appl. Phys. Lett. 1987, 51, 913), these devices have been developed further particularly with regard to the emitter materials used, and particular interest has been attracted in the last few years by what are called triplet emitters or else phosphorescent emitters.

OLEDs are generally implemented in layer structures. For better understanding, FIG. 1 shows a basic structure of an OLED. Owing to the application of external voltage to a transparent indium tin oxide (ITO) anode and a thin metal cathode, the anode injects positive holes, and the cathode negative electrons. These differently charged charge carriers pass through intermediate layers, which may also consist of hole or electron blocking layers not shown here, into the emission layer. The oppositely charged charge carriers meet therein at or close to doped emitter molecules, and recombine. The emitter molecules are generally incorporated into matrices consisting of small molecules or polymer matrices (in, for example, 2 to 10% by weight), the matrix materials being selected so as also to enable hole and electron transport. The recombination gives rise to excitons (=excited states), which transfer their excess energy to the respective electroluminescent compound. This compound can then be converted to a particular electronic excited state, which is then converted very substantially and with substantial avoidance of radiationless deactivation processes to the corresponding ground state by emission of light.

With a few exceptions, the electronic excited state, which can also be formed by energy transfer from a suitable precursor exciton, is either a singlet or triplet state, consisting of three sub-states. Since the two states are generally occupied in a ratio of 1:3 on the basis of spin statistics, the result is that the emission from the singlet state, which is referred to as fluorescence, leads to maximum emission of only 25% of the excitons produced. In contrast, triplet emission, which is referred to as phosphorescence, exploits and converts all excitons and emits them as light (triplet harvesting) such that the internal quantum yield in this case can reach the value of 100%, provided that the additionally excited singlet state, which is above the triplet state in terms of energy, relaxes fully to the triplet state (intersystem crossing, ISC), and radiationless competing processes remain insignificant. Thus, triplet emitters, according to the current state of the art, are more efficient electroluminophores and are better suitable for ensuring a high light yield in an organic light-emitting diode.

The triplet emitters suitable for triplet harvesting used are generally transition metal complexes in which the metal is selected from the third period of the transition metals. This predominantly involves very expensive noble metals such as iridium, platinum or else gold. (See also H. Yersin, Top. Curr. Chem. 2004, 241, 1 and M. A. Baldo, D. F. O'Brien, M. E. Thompson, S. R. Forrest, Phys. Rev. B 1999, 60, 14422). The prime reason for this is the high spin-orbit-coupling (SOC) of noble metal central ions (SOC constants Ir(III): ≈4000 cm$^{-1}$; Pt(II): ≈4500 cm$^{-1}$; Au(I): ≈5100 cm−1; Ref.: S. L. Murov, J. Carmicheal, G. L. Hug, Handbook of Photochemistry, 2nd Edition, Marcel Dekker, New York 1993, p. 338 ff). Due to this quantum mechanical characteristic, the triplet-singlet transition, which is without SOC strictly forbidden for optical transitions, is allowed and an emission decay time of a few µs, small enough for OLED applications is achieved.

Economically, it would be advantageous to replace the expensive noble metals with less expensive metals. Moreover, a large number of OLED emitter materials known to date are ecologically problematic, so that the use of less toxic materials is desirable, such as copper(I) complexes. At the same time, such complexes have much smaller SOC values (SOC constants of Cu(I): ≈850 cm$^{-1}$, Ref.: S. L. Murov, J. Carmicheal, G. L. Hug, Handbook of Photochemistry, $2^{nd}$ Edition, Marcel Dekker, New York 1993, p. 338 ff), as the central ions mentioned above. Therefore, the very important triplet-singlet-transitions of Cu(I)-complexes would be relatively strongly forbidden, and emission lifetimes, which is in the range of a few 100 µs to ms, would be too long. Such high emission decay times give rise to saturation effects with increasing current densities and the resulting occupation of a majority of or all emitter molecules. Consequently, further charge carrier streams can no longer lead completely to the occupation of the excited and emitting states. The result is then unwanted ohmic losses. This leads to a distinct decline in efficiency of the OLED device with rising current density (called "roll-off" behavior). The effects of triplet-triplet annihilation and of self-quenching are similarly unfavorable (see, for example, H. Yersin, "Highly Efficient OLEDs with Phosphorescent Materials", Wiley-VCH, Weinheim 2008 and S. R. Forrest et al., Phys. Rev. B 2008, 77, 235215). For instance, disadvantages are found particularly in the case of use of emitters with long emission lifetimes for OLED illuminations where a high luminance, for example of more than 1000 cd/m$^2$, is required (cf.: J. Kido et al. Jap. J. Appl. Phys. 2007, 46, L10.). Furthermore, molecules in electronically excited states are frequently more chemically reactive than in ground states so that the likelihood of unwanted chemical reactions increases with the length of the emission lifetime. The occurrence of such unwanted chemical reactions has a negative effect on the lifetime of the device.

Furthermore, Cu(I)-complexes undergo strong geometry changes after the excitation (through electron-hole recombination or through optical excitation) which leads to the reduction of emission quantum yields. Also, the emission colors are shifted due to these processed towards red, which is unwanted.

Moreover, many of the known copper-complexes are not soluble in the solvents that are needed for technical use. This is another aspect why the use of such complexes is disfavored.

It was the object underlying the present invention to provide new materials on the basis of copper(I) complexes, that do not exhibit the disadvantages described above.

DESCRIPTION OF THE INVENTION

Surprisingly, the object of the invention is met by the Cu(I) compounds described herein. In other words, the invention pertains to the creation and provision of novel Cu(I) compounds with the following characteristics:

Relatively short emission decay times of only a few µs,
High emission quantum yields of greater 40%,
Prevention of unwanted changes of geometry to a large extent, and
Solubility in different solvents that satisfy the technological requirements.
Organic solvents of the invention are
alkanes, also halogenated alkanes like pentane, hexane, heptane, including branched alkanes,
dichloromethane, chloroform, 1,2-dichlorethane, 1,1,1-trichlorethane, carbon tetrachloride, perchloroethylene
aromatic hydrocarbons, also halogenated: benzene, toluol, chlorobenzene 1,2-dichlorobenzene
Ethers: tetrahydrofuran, diethylether
Ketones: acetone, methyl ethyl ketone
as well as: acetonitrile, nitromethane, dimethyl sulfoxide, dimethyl formamide, methanol, ethanol and ethyl acetate.

In a preferred embodiment of the invention, the copper(I)-complex in well-soluble in at least one of the following solvents: polar hydrocarbons like, for example, dichlormethane, chloroform, 1,2-dichlorethane, 1,1,1-trichlorethane, perchloroethylene, toluol, chlorbenzene, 1,2-dichlorobenzene, tetrahydrofuran, diethylether, acetone, methyl ethyl ketone, nitromethane, dimethylsulfoxide, dimethylformamide, methanol, and ethanol.

Singlet Harvesting

It is of particular importance to loosen the forbidden transition prohibition from the excited triplet state $T_1$ to the singlet state $S_0$ in order to develop emitter molecules with shortest possible emission decay times, yet high emission quantum yields. OLEDs using such emitters show a markedly diminished roll-off behavior of efficiency and provide for a longer operating life of the optoelectronic device.

The object described above is met by the present invention by using emitter molecules that have particular electronic structures or singlet-triplet-energy differences and that show, according to the invention, the singlet-harvesting effect, which is described here for the first time for Cu(I)-complexes. In FIG. 2a, a diagram of energy levels for transition metal complexes is depicted with spin orbit coupling that is either small or has only a small effect (e.g. metal complexes of the first period of the transition metals or metal complexes with ligand-centered triplet states). The photo-physical electroluminescence properties of these molecules are described with reference to this diagram. Hole-electron recombination, as occurs, for example, in an optoelectronic device, leads, on statistical average, to 25% occupation of the singlet state (1 singlet path) and to 75% occupation of the three sub-states of the triplet state (3 triplet paths) that lye at $\Delta E_1(S_1-T_1)$ below. The excitation into the $S_1$ state relaxes due to the intersystem crossing (ISC) process, which generally is faster than $10^{-12}$ s in transition metal complexes, into the $T_1$ state. The radiative emission decay time of the triplet stat is very long for these metal complexes of the first period of the transition metals (e.g., 100 µs to 1000 µs or longer).

According to the invention, the disadvantages of the state of the art described above can be avoided by choosing Cu(I)-complexes that have an energy difference $\Delta E(S_1-T_1)$ between the lowest excited singlet state ($S_1$) and the triplet state ($T_1$) below it, of smaller than 2500 cm$^{-1}$. This is illustrated by the energy level diagram for Cu(I)-complexes shown in FIG. 2b. This energy difference is small enough to enable thermal repopulation of the $S_1$ state from the $T_1$ state according to a Boltzmann distribution, or according to the thermal energy $k_B T$. This process proceeds according to equation (1):

$$\text{Int}(S_1 \to S_0)/\text{Int}(T_1 \to S_0) = k(S_1)/k(T_1) \exp(-\Delta E(S_1-T_1)/k_B T) \quad (1)$$

In this equation, $\text{Int}(S_1 \to S_0)/\text{Int}(T_1 \to S_0)$ is the intensity ratio of the emissions from the $S_1$ state and the $T_1$ state. $k_B$ is the Boltzmann constant and T the absolute temperature. $k(S_1)/k(T_1)$ is the rate ratio of the respective conversion processes to the electronic ground state $S_0$. For Cu(I)-complexes, this ratio is between $10^2$ and $10^4$. Preferred in accordance with the invention are molecules having a rate ratio of about $10^3$ to $10^4$. $\Delta E$ represents the energy difference $\Delta E_2(S_1-T_1)$ according to FIG. 2b.

The process of thermal repopulation described herein opens up an emission channel via the singlet state $S_1$ from the populated triplet. Since the transition from the $S_1$ to the $S_0$ state is strongly allowed, the triplet excitation energy is obtained virtually completely as light emission via the singlet state. The smaller the energy difference $\Delta E$, the more marked this effect is. Preference is therefore given to Cu(I)-complexes having a $\Delta E = \Delta E(S_1-T_1)$ value between the lowermost excited singlet state and the triplet state below it of less than 1500 cm$^{-1}$, preferably less than 1000 cm$^{-1}$, more preferably of less than 500 cm$^{-1}$.

This effect is to be illustrated by a numerical example. Given a typical energy difference of $\Delta E=800$ cm$^{-1}$, for room temperature applications (T=300 K) with $k_B T=210$ cm$^{-1}$ and a rate ratio of $10^8$, an intensity ratio of the singlet to triplet emission according to equation (1) of approximately 20 is obtained. This means that the singlet emission process is dominant to an extreme degree for a molecule having these example values.

The emission lifetime of this example molecule also changes as a result. The thermal repopulation results in a mean lifetime $\tau_{av}$. This can be described by equation (2)

$$\tau_{av} \approx \tau(S_1) \cdot \exp(\Delta E(S_1-T_1)/k_B T) \qquad (2)$$

In this equation, $\tau(S_1)$ is the fluorescence lifetime without repopulation and $\tau_{av}$ is the emission lifetime, which is determined on opening of the repopulation channel by the two states $T_1$ and $S_1$ (see FIG. 2b). The other parameters have been defined above.

Equation (2) is again to be illustrated by a numerical example. For the assumed energy difference of $\Delta E=800$ cm$^{-1}$ and a decay time of the fluorescing $S_1$ state of 50 ns, an emission decay time (of the two states, i.e. of the $S_1$ state thermally repopulated from the $T_1$ state) of $\tau_{av} \approx 2$ μs is obtained. This decay time is shorter than those of very good Ir(III) or Pt(II) triplet emitters.

In summary, using this singlet harvesting process for Cu(I)-complexes, it is thus possible in the ideal case to capture virtually all, i.e. a maximum of 100%, of the excitons and convert them to light via singlet emission. In addition, it is possible to shorten the emission decay time well below the value for pure triplet emitters of Cu(I)-complexes, which is generally a few hundred μs to ms. Therefore, the use according to the invention of the respective complexes is particularly suitable for optoelectronic devices.

The Cu(I)-complexes according to the invention having the above-described properties, i.e. having a small singlet-triplet energy difference $\Delta E(S_1-T_1)$, are preferably described with the general formula A given below. The electronic transitions that govern the optical properties of these Cu(I)-complexes show a pronounced metal to ligand charge transfer character. This transition type correlates with a relatively small value of the quantum-mechanical exchange integral, which is known to a person of skill in the art. This results in the desired small energy difference $\Delta E(S_1-T_1)$.

The invention refers in another aspect to a method for selecting copper(I) complexes, whose $\Delta E(S_1-T_1)$-value between the lowest excited singlet state $(S_1)$ and the triplet state $(T_1)$ below it is smaller than 2500 cm$^{-1}$, preferably smaller than 1500 cm$^{-1}$, particularly preferred smaller than 1000 cm$^{-1}$, most preferred smaller than 500 cm$^{-1}$.

The determination of the $\Delta E(S_1-T_1)$ value can either be performed by quantum-mechanical calculations using computer programs known in the art (for example, using Turbomole programs executing TDDFT calculations with reference to CC2 calculations) or determined experimentally, as explained below.

The energy difference $\Delta E(S_1-T_1)$, more particularly of the complexes described by formula A can be described as an approximation by quantum-mechanical means via the exchange integral multiplied by the factor 2. The value of the latter depends directly on the so-called charge-transfer-character under participation d-orbitals of the metal and the π*-orbitals of the ligands. This means that an electronic transition between the different molecular orbitals represents a charge transfer (CT) process. The smaller the overlap of the above-described molecular orbitals, the more marked is the electronic charge transfer character. This is then associated with a decrease in the exchange integral and hence a decrease in the energy difference $\Delta E(S_1-T_1)$. Due to these photo-physical (quantum-mechanical) properties, it is possible to achieve the inventive energy differences with $\Delta E(S_1-T_1)$ of less than 2500 cm$^{-1}$ or less than 1500 cm$^{-1}$ or less than 1000 cm$^{-1}$ or even less than 500 cm$^{-1}$.

The $\Delta E(S_1-T_1)$ value can be determined experimentally as follows:

For a given Cu(I)-complex, the energy difference $\Delta E(S_1-T_1)=\Delta E$ can be determined in a simple manner using the above-specified equation (1). A rearrangement gives:

$$\ln\{\text{Int}(S_1 \rightarrow S_0)/\text{Int}(T_1 \rightarrow S_0)\} = \ln\{k(S_1)/k(T_1)\} - (\Delta E(S_1-T_1)/k_B)(1/T) \qquad (3)$$

For the measurement of the intensities Int($S_1 \rightarrow S_0$) and Int($T_1 \rightarrow S_0$), it is possible to use any commercial spectrophotometer. A graphic plot of the (logarithmized) intensity ratios $\ln\{\text{Int}(S_1 \rightarrow S_0)/\text{Int}(T_1 \rightarrow S_0)\}$ measured at different temperatures against the reciprocal of the absolute temperature T generally gives a straight line. The measurement is conducted within a temperature range from room temperature (300 K) to 77 K or to 4.2 K, the temperature being established by means of a cryostat. The intensities are determined from the (corrected) spectra, Int($S_1 \rightarrow S_0$) and Int($T_1 \rightarrow S_0$) representing, respectively, the integrated fluorescence and phosphorescence band intensities, which can be determined by means of the programs provided with the spectrophotometer. The respective transitions (band intensities) can be identified easily since the triplet band is of lower energy than the singlet band and gains intensity with falling temperature. The measurements are conducted in oxygen-free diluted solutions (approx. 10$^{-2}$ mol L$^{-1}$) or on thin films of the corresponding molecule or on films doped with the corresponding molecules. If the sample used is a solution, it is advisable to use a solvent or solvent mixture which forms glasses at low temperatures, such as 2-methyl-tetrahydrofuran, butyronitrile, toluol, ethanol or aliphatic hydrocarbons. If the sample used is a film, the use of a matrix having a much greater singlet and triplet energy than that of the Cu(I)-complexes (emitter molecules), for example PMMA (polymethyl methacrylate), is suitable. This film can be applied from solution.

The slope of the straight line is $-\Delta E/k_B$. With $k_B=1.380 \cdot 10^{-23}$ JK$^{-1}$=0.695 cm$^{-1}$ K$^{-1}$, it is possible to determine the energy separation directly.

A simple, approximate estimation of the $\Delta E(S_1-T_1)$ value can also be made by recording the fluorescence and phosphorescence spectra at low temperature (e.g. 77 K or 4.2 K using a cryostat). The $\Delta E(S_1-T_1)$ value then corresponds approximately to the energy difference between the high-energy slope flanks of the fluorescence and phosphorescence bands.

Another method for determining the $\Delta E(S_1-T_1)$-value is through measuring the emission decay time $\tau_{av}$ with an instrument that is commercially available. Herein, the emission decay time is measured using a cryostat for the range between 4.2 K or, e.g., 20 K and 300 K. Using formula (4) and the emission decay time measured at low temperature for the triplet state $\tau(T_1)$, a fit of the measured values can be performed according to formula (4), yielding the $\Delta E(S_1-T_1)$-value. (Note: The $\tau(T_1)$-value is often represented by the plateau that might be seen when the measured values are plotted. In case such a plateau is seen, cooling to 4.2 K is generally not necessary. An example is given in FIG. 8.)

$$\tau_{av} = \frac{1 + \exp\left(-\frac{\Delta E(S_1 - T_1)}{k_B T}\right)}{\frac{1}{\tau(T_1)} + \frac{1}{\tau(S_1)} \exp\left(-\frac{\Delta E(S_1 - T_1)}{k_B T}\right)} \quad (4)$$

The more pronounced the CT character of an organic molecule, the more the electronic transition energies change as a function of solvent polarity. Therefore, a strong polarity dependence of the emission energies provides an indication of small $\Delta E(S_1 - T_1)$ values.

Stabilization of the Molecular Structure

Quadruply coordinated Cu(I)-complexes show an almost tetrahedral coordination of the metal atom in the electronic ground state.

When transitioning into an electronic excited state with pronounced metal-to-ligand charge-transfer character, the metal atom is formally oxidized to Cu(II), and a relevant change of the geometry towards a quadratic-planar coordination occurs, which can be called a "planarization" of the complex. This process provides for a very effective mechanism for quenching luminescence.

In the copper(I) complexes of the invention, this quenching mechanism is prevented or strongly reduced by the presence of a sterically demanding substituent at the diimine ligand N∩N (in particular in positions 2 and 9 of 1,10-phenanthroline or in positions 3 and 3' of 2,2'-bipyridine) by a hindrance of change of geometry at the Cu atom. At the same time, such substitutions help prevent nucleophilic reactions with the Cu center (with solvents, contaminants, easily coordinating matrix material). Already a methyl group leads to a stiffening of the resulting Cu complexes. A sterically demanding substituent therefore is, besides methyl, an alky group —$(CH_2)_n$—$CH_3$ (n=0-20) (also branched), an aryl group with 6-20 carbon atoms (e.g. -Ph), alkoxy groups —O—$(CH_2)_n$—$CH_3$ (n=0-20), an aryloxy group (e.g. —OPh) or a silane group (e.g. —$SiMe_3$). The alkyl and aryl groups can also be substituted (e.g. with halogens, alkoxy or silane groups, etc.) or lead to annelated ring systems (see example 2).

Chemical Lead

The emitter A comprises the following features:

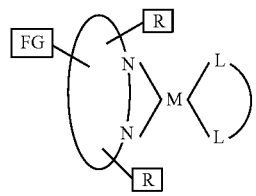

Formula A

M is Cu(I).

L∩L is a singly negatively charged, bidentate ligand.

The ligand N∩N is a substituted diimine ligand, in particular a substituted 2,2'-bipyridine derivative (bpy) or 1,10-phenanthroline derivative (phen).

R is a sterically demanding substituent in 3,3'-position (bpy) or 2,9-position (phen) that prevents a change of geometry towards a planarization of the complex in the excited state. A sterically demanding substituent is, in particular, an alkyl group —$(CH_2)_n$—$CH_3$ (n=0-20) (also branched), an aryl group with 6-20 carbon atoms (e.g. -Ph), alkoxy group —O—$(CH_2)_n$—$CH_3$ (n=0-20), an aryloxy group (e.g. —OPh) or a silane group (e.g. —$SiMe_3$). The alkyl and aryl groups can also be substituted (e.g. with halogens, alkoxy or silane groups, etc.) or lead to annelated ring systems. Although two groups R are shown in formula A, a complex of the invention can also contain only one group R in one embodiment of the invention.

The FG=function group is a further substituent that provides for an additional function of the complex, The function groups FG are attached to the diimine substituents either directly or via appropriate bridges (see below).

The function group can be a group with the characteristics of an electron conductor.

The function group can be a group comprising the characteristics of a hole conductor.

The function group can be a group that affects the solubility of the complex.

Diimine Ligands

The diimine ligand is preferably either a 2,2'-bipyridine or a substituted 1,10-phenanthroline ligand. The syntheses of different, substituted bpy and phen ligands have repeatedly been described in the scientific literature (G. Chelucci, R. P. Thummel, Chem. Rev. 2002, 102, 3129; C. Kaes, A. Katz, M. W. Hosseini, Chem. Rev. 2000, 100, 3553; M. Schmittel, H. Ammon, Eur. J. Inorg. Chem. 1998, 785. M. Heller, U. S. Schubert J. Org. Chem. 2002, 67, 8269.) and are known to those skilled in the art.

Substituted 2,2'-Bipyridine ligands

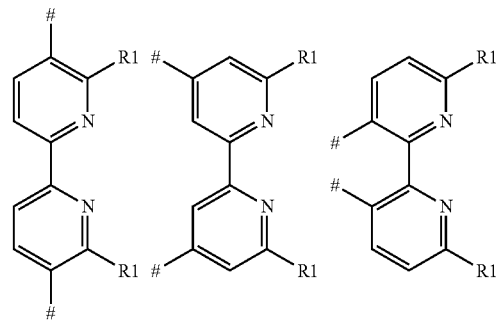

The substituent R1 can be an alkyl group [$CH_3$—$(CH_2)_n$—] (n=1-20) that can be branched or substituted with halogens or an aryl group (in particular phenyl) that can be substituted with alkyl groups, halogens (F, Cl, Br, I), silane (—$SiR'_3$) or ether groups —OR' (R' defined as R1).

At the positions "#", the diimine ligand is substituted with a function group FG. The attachment of the function groups described below also occurs at the positions marked with a "#" (see below). The binding between the function group and the diimine ligand can occur, on the one hand, at the positions "#". This way, direct $C_{FG}$—$C_{NN}$ bonds are formed, wherein $C_{NN}$ represents the C-atom of the diimine ligand that is marked with "#", and $C_{FG}$ represents the C-atom of the function group. When the atom marked with "#" is a nitrogen atom, $N_{FG}$—$C_{NN}$ bonds result, wherein $N_{FG}$ represents the nitrogen atom marked with "#". On the other hand, the function group can be bound via a bridge to the diimine ligand, wherein, e.g., ether, thioether, ester, amide, methylene, silane, ethylen, ethine bridges are possible. Based on this, the following are examples for bridges: $C_{FG}$—O—$C_{NN}$, $C_{FG}$—S—$C_{NN}$, —$C_{FG}$—C(O)—O—$C_{NN}$—, $C_{FG}$—C(O)—NH—

$C_{NN}$—, $C_{FG}$—$CH_2$—$C_{NN}$, $C_{FG}$—$SiR'_2$—$C_{NN}$, $C_{FG}$—CH=CH—$C_{NN}$, $C_{FG}$—C≡C—$C_{NN}$, $N_{FG}$—$CH_2$—$C_{NN}$.

The methods for binding the function groups to the diimine ligand, either directly or via a bridge, are known to a person of skill in the art (Suzuki-, Still-, Heck-, Sonogashira-, Kumuda-, Ullmann-, Buchwald-Hartwig-coupling and their variants; (thio)etherification, esterification, nucleophilic and electrophilic substitution at the $sp^3$ carbon or aromatic compounds, etc.). The ligand (4,4'-bis(5-(hexylthio)-2,2'-bithien-5'-yl)-2,2'-bipyridine) that is described in the literature illustrates an example for the binding of an electron conduction substituent to the bpy liganden via a Stille coupling (C.-Y. Chen, M. Wang, J.-Y. Li, N. Pootrakulchote, L. Alibabaei, C.-h. Ngoc-le, J.-D. Decoppet, J.-H. Tsai, C. Grätzel, C.-G. Wu, S. M. Zakeeruddin, M. Grätzel, ACS Nano 2009, 3, 3103).

A further possibility for synthesizing substituted bpy is the coupling of two substituted pyridines that are already substituted with the group R and the function group. The bpy ligand resulting therefrom can therefore also be substituted in a symmetrical manner. The methods and relevant literature is summarized in the review article by G. Chelucci (G. Chelucci, R. P. Thummel, Chem. Rev. 2002, 102, 3129).

In a particular embodiment, the group R1 can also be a substituent that conducts electrons, conducts holes or increases the solubility. This leads to the following diimine ligands:

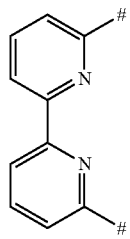

Substituted 1,10-phenanthroline ligands

The substituent R1 is an alkyl group [$CH_3$—$(CH_2)_n$—] (n=1-20) that can also be branched or substituted with halogens (F, Cl, Br, I) or an aryl group (in particular phenyl), that can be substituted with alkyl groups, halogens (F, Cl, Br, I), silane (—$SiR'_3$) or ether groups —OR' (R' defined such as R1).

For coupling the function group to the phenanthroline ligand, those methods can be used that have already been described with reference to the bpy-ligands:

At the positions marked with "#", the diimine ligand is substituted with a function group that is defined further below. Therein, the function group FG is bound to the diimine ligand either via $C_{FG}$—$C_{NN}$ or $N_{FG}$—$C_{NN}$ bonds (wherein $C_{FG}$=C-atom of the function group, $N_{FG}$=N-atom of the function group, $C_{NN}$=C-atom of the diimine ligand), or via a bridge, e.g. $C_{FG}$—O—$C_{NN}$, $C_{CF}$—S—$C_{NN}$, —$C_{FG}$—C(O)—O—$C_{NN}$, $C_{FG}$—C(O)—NH—$C_{NN}$, $C_{FG}$—$CH_2$—$C_{NN}$, $C_{FG}$—$SiR'_2$—$C_{NN}$, $C_{FG}$—CH=CH—$C_{NN}$, $C_{FG}$—C≡C—$C_{NN}$, $N_{FG}$—$CH_2$—$C_{NN}$. The methods for binding the function group to the diimine ligand, either directly or via a bridge, are known to a person of skill in the art. The examples 1-9 illustrate the possibilities for synthesizing the substituted phen ligand.

In an embodiment of the invention, the rest R1 is an electron conducting, hole conducting, or solubility-increasing substituent. The leads to the following diimine ligands:

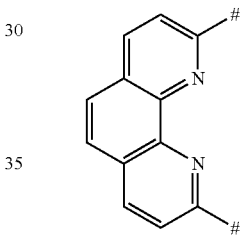

Other Diimine Ligands

The diimine ligand can also be chosen from the following molecules:

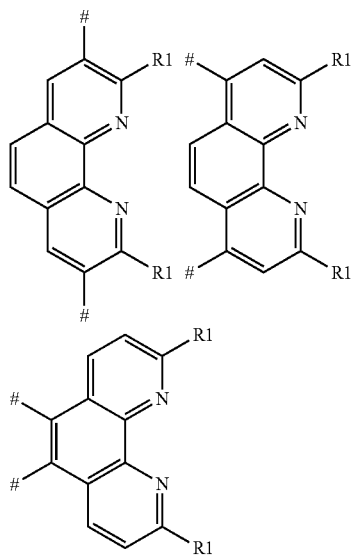

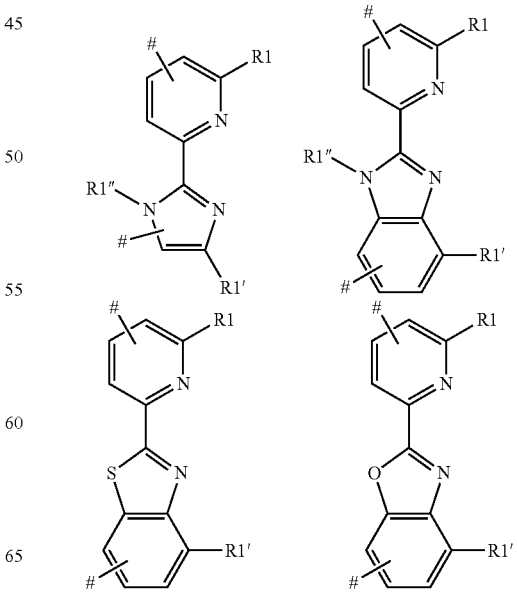

-continued

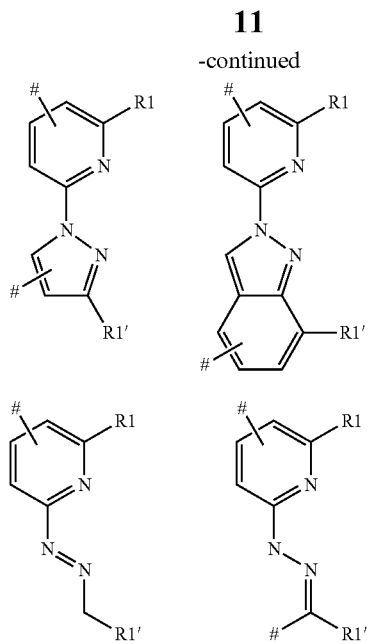

wherein the substituents R1, R1' and R1" are an alkyl group [CH$_3$—(CH$_2$)$_n$—] (n=1-20), that can also be branched or substituted with halogens (F, Cl, Br, I), or an aryl group (in particular phenyl), that can be substituted with alkyl groups, halogens (F, Cl, Br, I), silane (—SiR'$_3$) or ether groups —OR' (R' defined like R1, R1' or R1"). Substituents # are as defined above (bpy and phen ligands).

DEFINITION OF THE L∩L LIGANDS

The singly negatively charged ligand L∩L can be one of the following molecules:

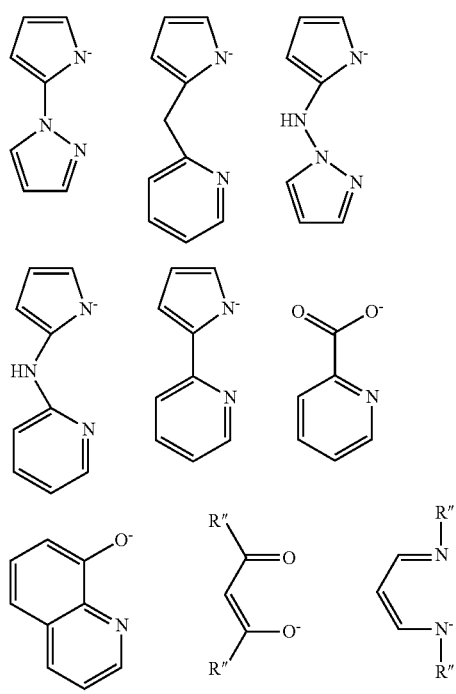

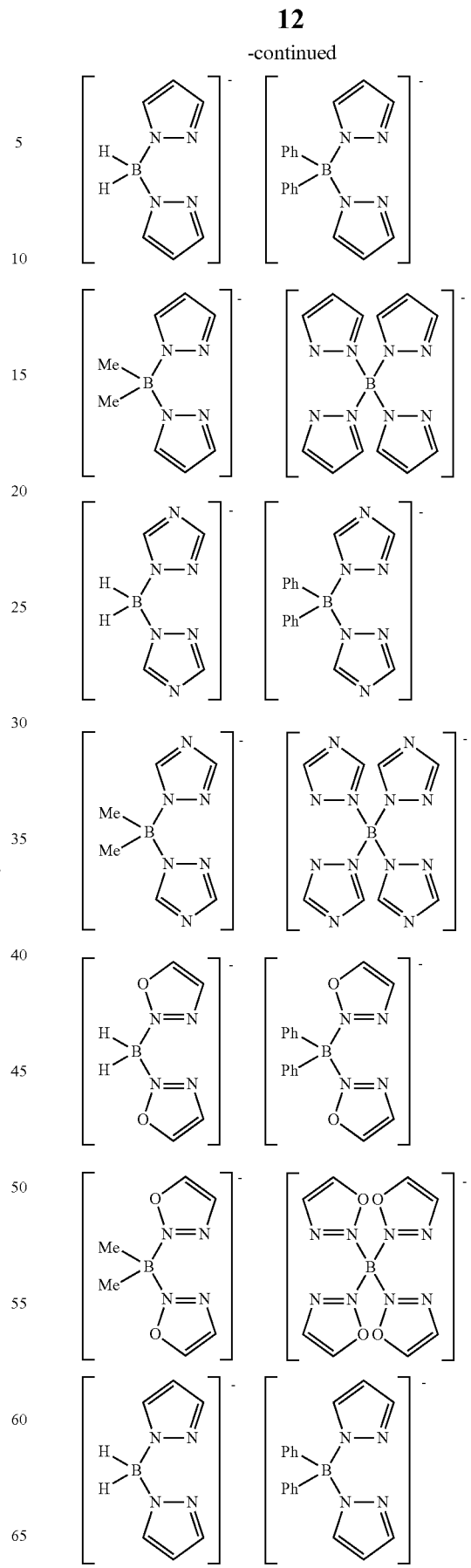

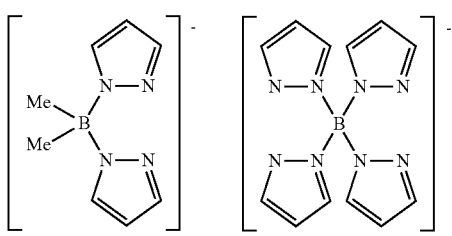
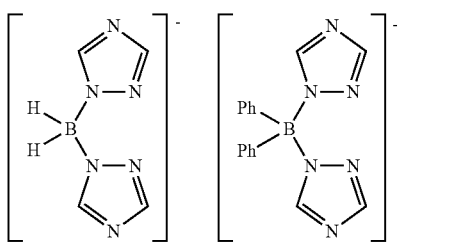
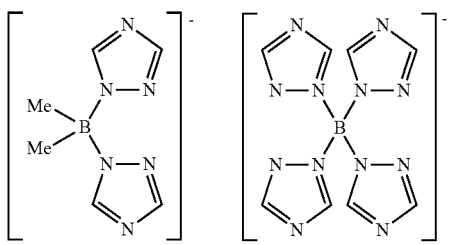
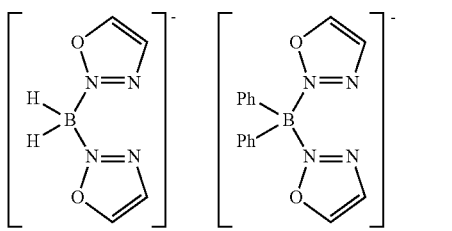
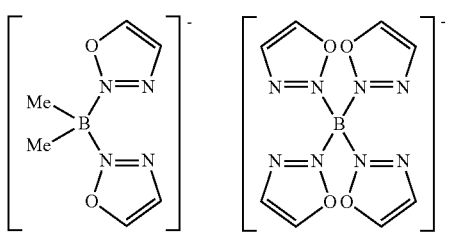
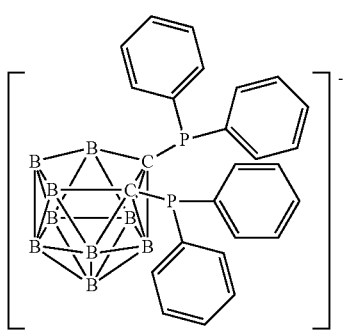
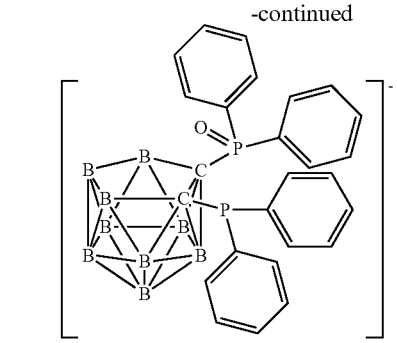
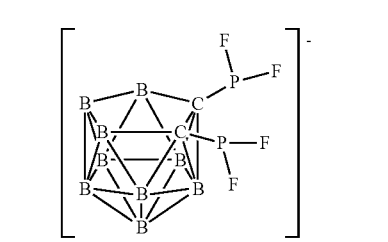
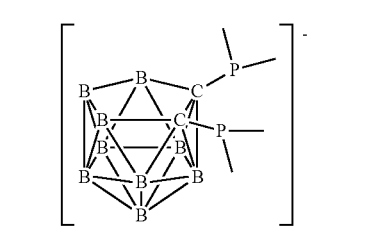
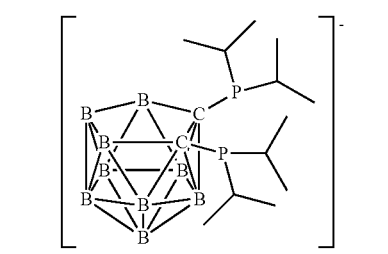
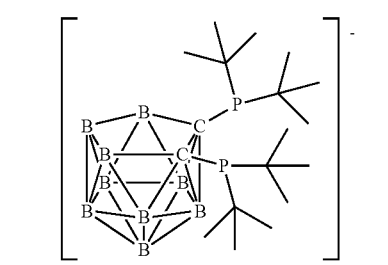
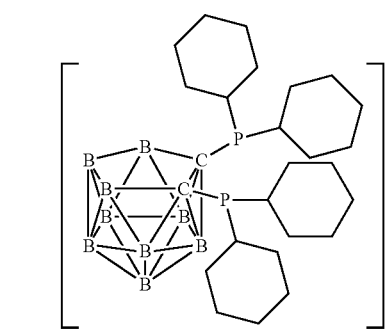

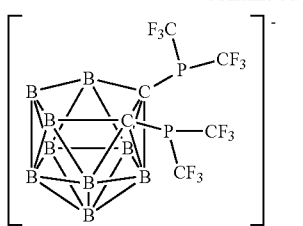
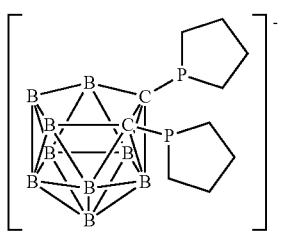
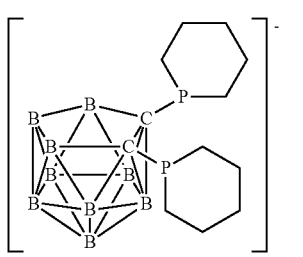
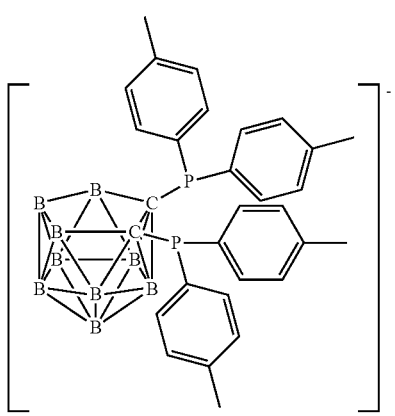
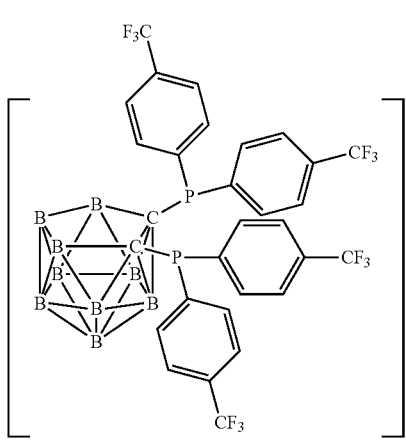
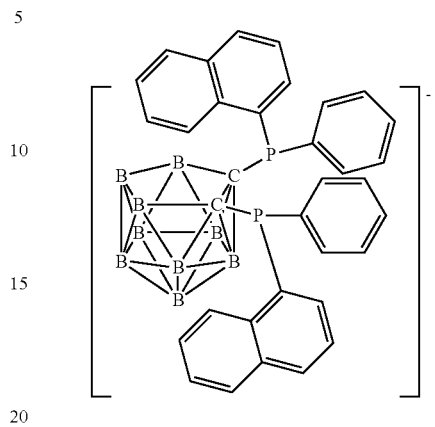
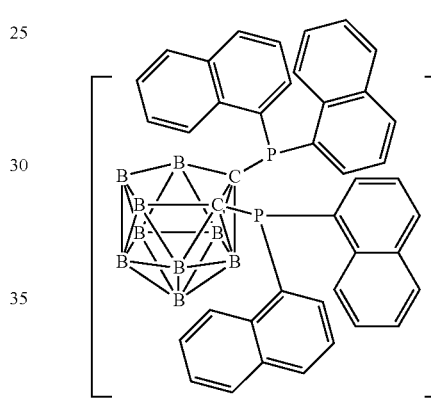
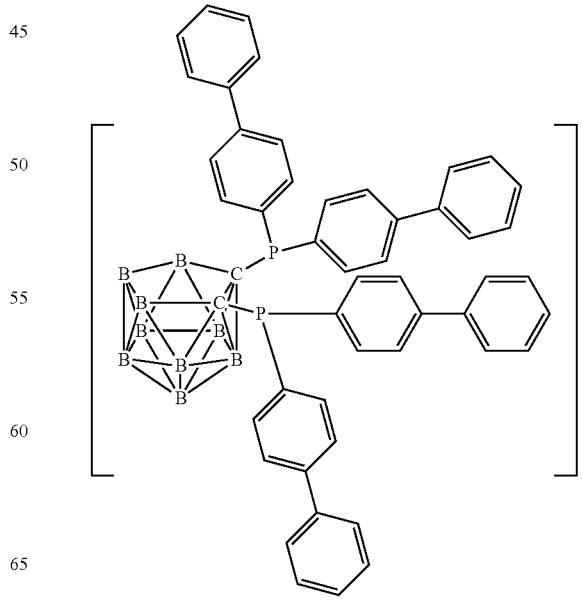

-continued

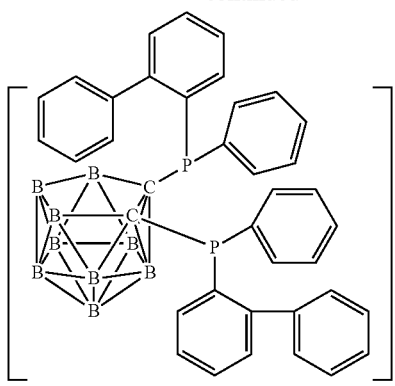

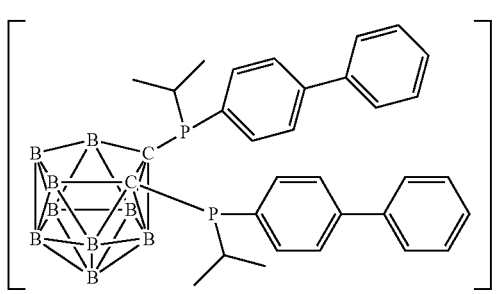

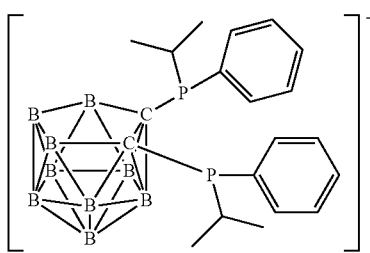

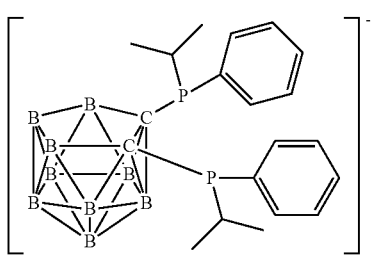

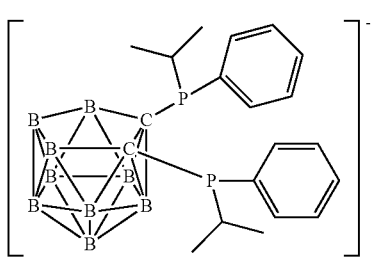

-continued

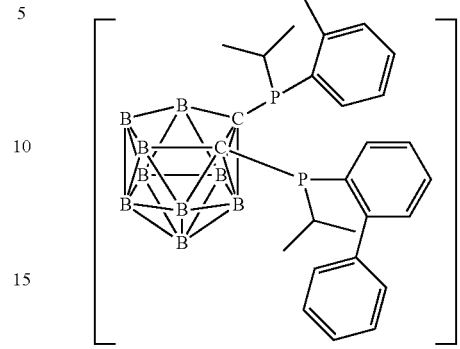

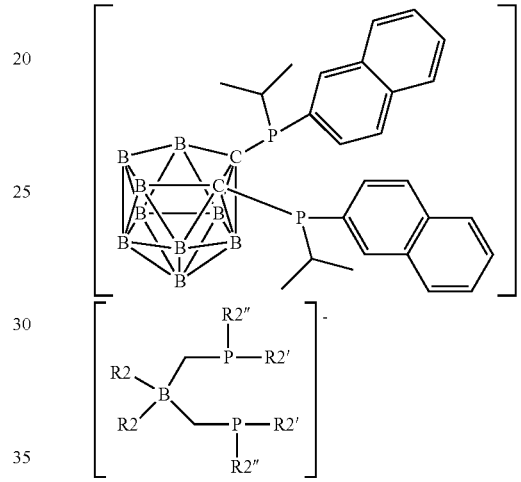

pop = [P₂O₅H₂]²⁻

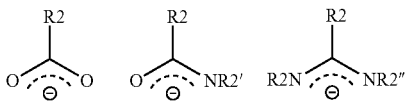

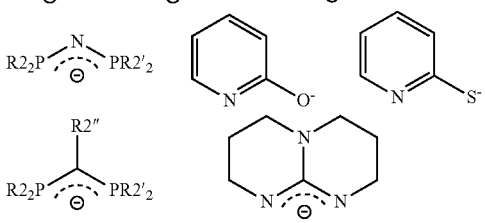

The substituents R2, R2' and R2" are alkyl groups [CH₃—(CH₂)ₙ—] (n=0-20) that can also be branched or substituted with halogens (F, Cl, Br, I), or aryl groups (in particular phenyl), that can be substituted with alkyl groups, halogens (F, Cl, Br, I), silane (—SiR'''₃) or ether halogens —OR''' (R''' defined as R2, R2' or R2").

DEFINITION OF THE FUNCTION GROUP FG

The function groups (FG) can be attached once or multiple times to the N∩N ligand. Identical or different function groups can be used. The function groups can be present in a symmetrical or asymmetrical way. Due to the synthesis pathway, a double-substitution of identical function groups is usually preferred.

Electron Conductor

Since the electron conductor materials are exclusively aromatic compounds, a substitution is possible using conventional coupling reactions. As coupling reactions, Suzuki-, Still-, Heck-, Sonogashira-, Kumuda-, Ullmann-, Buchwald-Hartwig-couplings as well as their variants can be used.

A phen or bpy derivative substituted with an halogenide (Cl, Br, I), in particular Br, is reacted with a corresponding electron conducting material carrying a suitable leaving group. Preferred is a Suzuki-coupling using the corresponding arylboronic acids and esters as well as the Buchwald-Hartwig-coupling for generating aryl-N-bonds. Depending on the function group, further, common attachment reactions can also be used, e.g. via a bridge between function group FG and diimine ligand. In the presence of —OH groups, esterification and etherification may be used, with —NH$_2$ groups imine and amide formation, with —COOH groups esterification. The substitution pattern of the diimine must be adapted accordingly (see above under "Diimine Ligands"). Methods for attaching function groups are known to a person of skill in the art.

As an electron transport substituent, the following groups can for example be used, (attachment position of the bond is marked with an #).

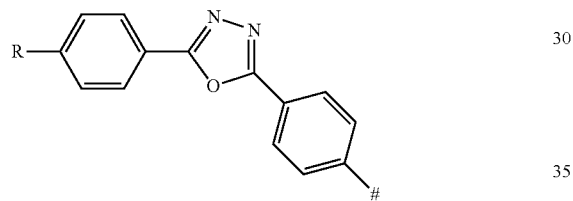

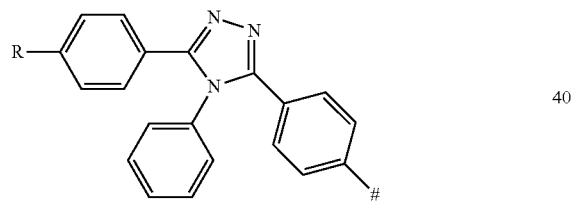

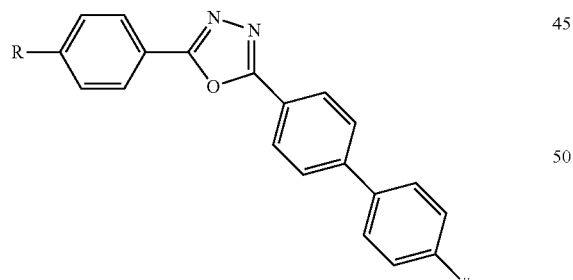

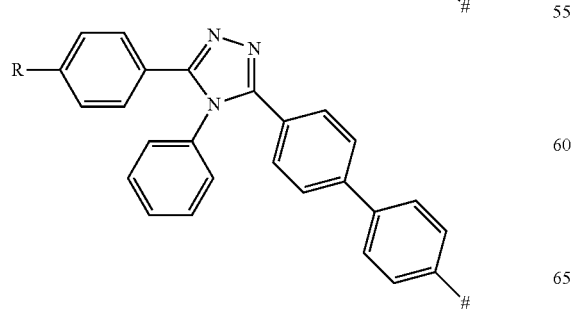

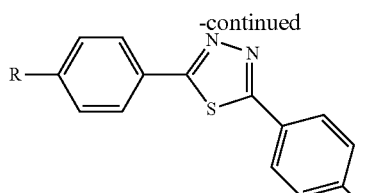

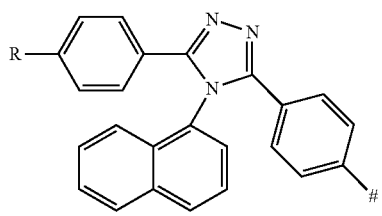

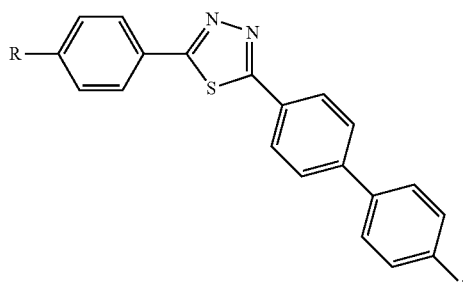

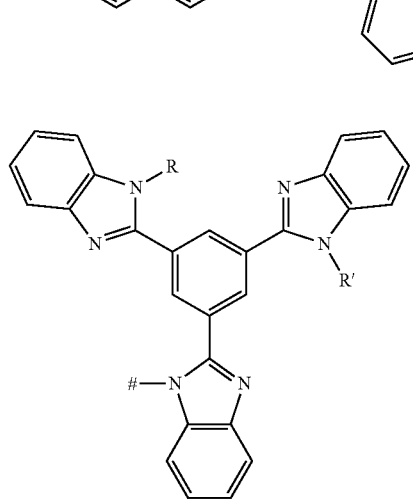

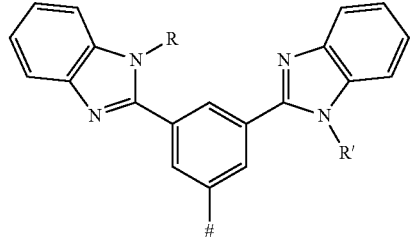

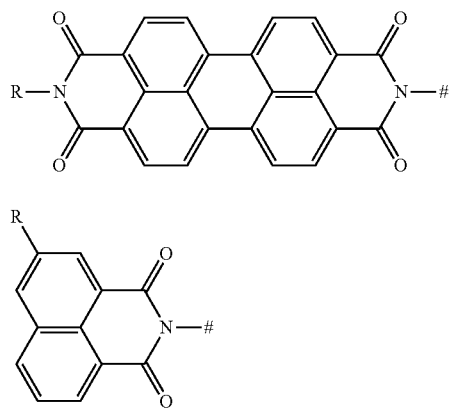

The substituents R and R' are alkyl [CH₃—(CH₂)ₙ—] (n=0-20), that can also be branched or substituted with halogens (F, Cl, Br, I), or an aryl group (in particular phenyl), that can be substituted with alkyl groups, halogens (F, Cl, Br, I), silane (—SiR'''₃) or ether groups —OR''' (R''' defined like R).

Hole Conductors

For the hole conductors, generally the analogous applies as for the electron conductor. The attachment of the hole conductor to the diimine ligand can most conveniently be realized through palladium-catalyzed coupling reactions; further attachments, also via a bridge, are also possible.

As hole transport substituents, the following groups can, for example, be used (attachments are realized at the positions marked with an #):

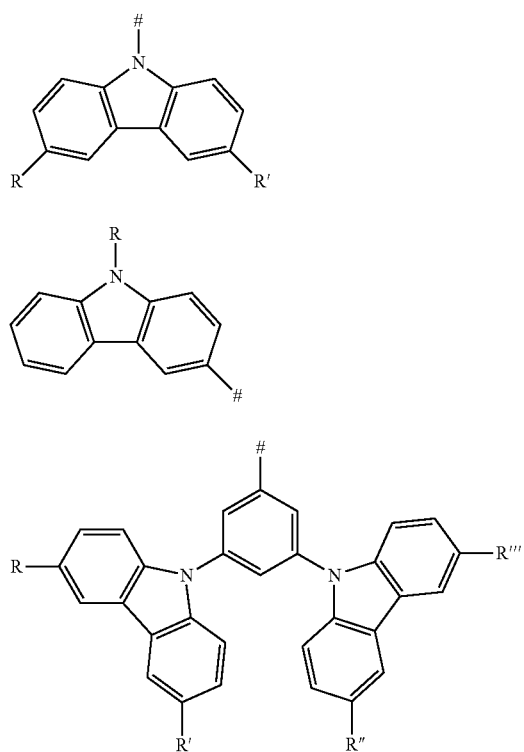

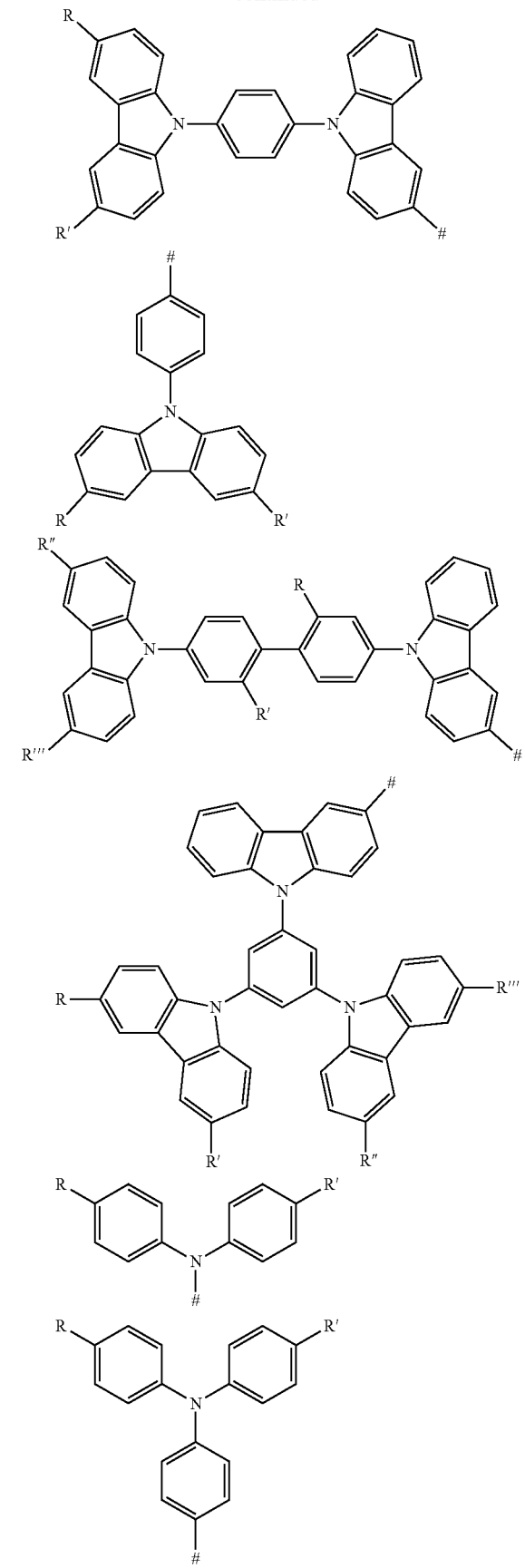

-continued
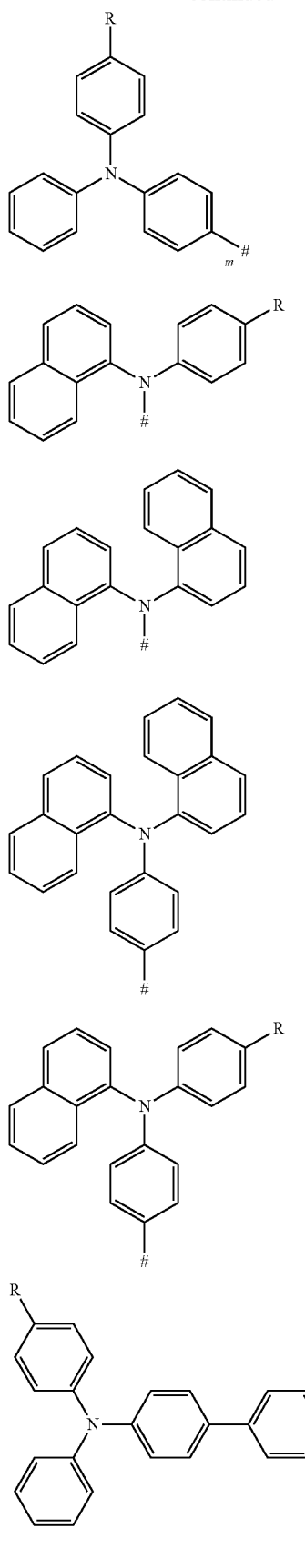
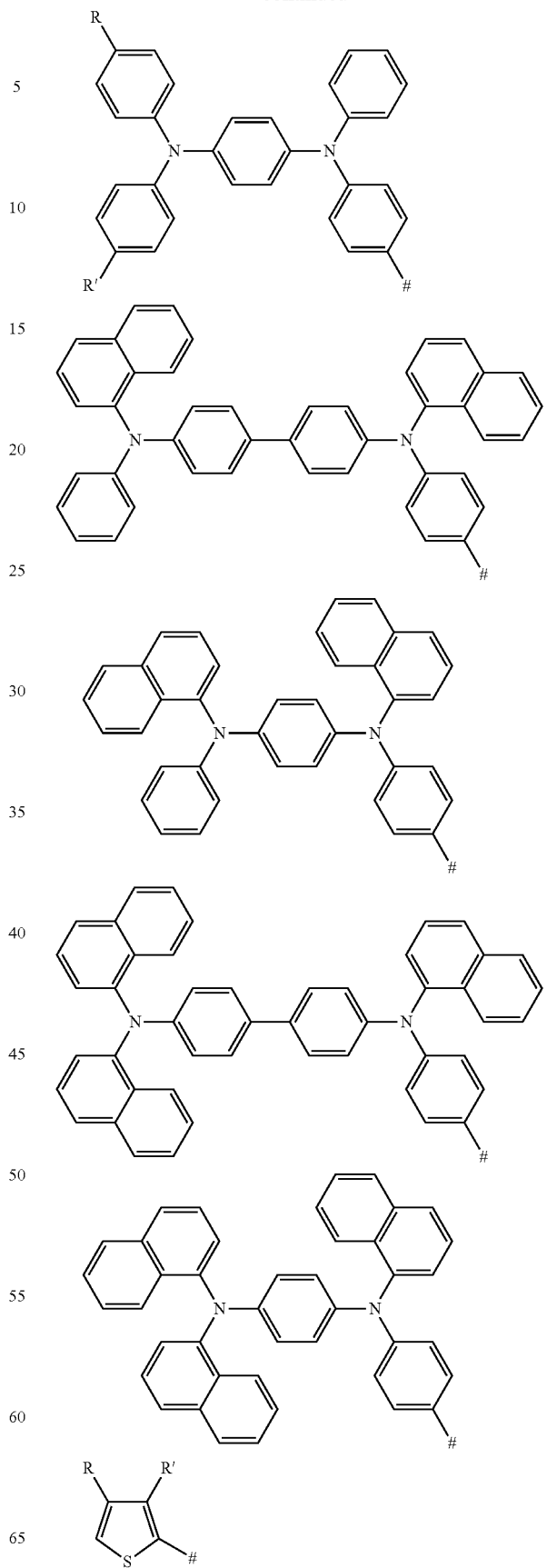

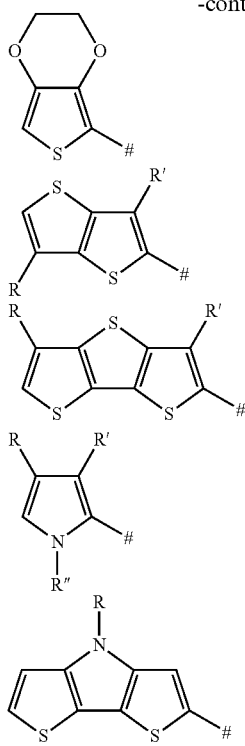

The substituents R, R" and R"' are alkyl [CH$_3$—(CH$_2$)$_n$—] (n=0-20), that can also be branched or substituted with halogens (F, Cl, Br, I), or aryl (in particular phenyl) that can be substituted with alkyl groups, halogens (F, Cl, Br, I), silane (—SiR""$_3$) or ether groups —OR"" (R"" defined like R).

Solubility

When manufacturing optoelectronic devices using wet-chemical processes, it is advantageous to specifically regulate the solubility. Thereby, the complete or partial dissolving of a layer already deposited can be avoided. By introducing special substituents, the solubility characteristics can be strongly influenced. Thereby, it is possible to use orthogonal solvents that dissolve only the substance of the instant manufacturing step, but not the substances of the layer(s) below.

Solubility in Nonpolar Media

Nonpolar function groups FG increase the solubility in nonpolar solvents and decrease the solubility polar solvents. Nonpolar groups are, e.g. alkyl groups [CH$_3$—(CH$_2$)$_n$—] (n=1-30), also branched, substituted alkyl groups, e.g. with halogens. In particular: partially or perfluorinated alkyl groups as well as perfluorinated oligo- and polyethers, e.g. [—(CF$_2$)$_2$—O]$_n$— and (—CF$_2$—O)$_n$— (n=2-500). Further nonpolar groups are: ether —OR, thioether —SR, differently substituted silanes R$_3$Si—(R=alkyl or aryl), siloxanes R$_3$Si—O—, oligosiloxanes R'(—R$_2$Si—O)$_n$— (R'=R, n=2-20), polysiloxane R'(—R$_2$Si—O)$_n$— (n>20); oligo/polyphosphazene R'(—R$_2$P=N—)$_n$— (n=1-200).

Solubility in Polar Media

Polar function groups increase the solubility in polar media, such as:

Alcohol groups: —OH

Thioalkohols —SH

Carboxylic acids, phosphonic acids, sulfonic acid groups as well as their salts and esters (R=H, alkyl, aryl, halogen; cations: alkali metals, ammonium salts):

—COOH, —P(O)(OH)$_2$, —P(S)(OH)$_2$, —S(O)(OH)$_2$, —COOR, —P(O)(OR)$_2$, —P(S)(OR)$_2$, —S(O)(OR)$_2$, —CONHR, —P(O)(NR$_2$)$_2$, —P(S)(NR$_2$)$_2$, —S(O)(NR$_2$)$_2$

Sulfoxides: —S(O)R, —S(O)$_2$R

Carbonyl groups: —C(O)R

Amines: —NH$_2$, —NR$_2$, —N(CH$_2$CH$_2$OH)$_2$,

Hydroxylamines =NOR

Oligoesters, —O(CH$_2$O—)$_n$, —O(CH$_2$CH$_2$O—)$_n$ (n=2-200)

Positively charged substituents: e.g. ammonium salts —N$^+$R$_3$X$^-$, phosphonium salts —P$^+$R$_3$X$^-$ Negatively charged substituents: e.g. borate —(BR$_3$)$^-$, aluminate —(AlR$_3$)$^-$ (the anion can be an alkali metal or ammonium ion).

In order to avoid the presence of freely movable ions, positively and negatively charged substituents can be united in a function group FG.

Accordingly, the inventions refers in a further aspect to a method for manufacturing an optoelectronic device, in particular for wet-chemical manufacturing, wherein the method comprises the following steps:

Depositing a first emitter complex dissolved in a first solvent on a carrier, and depositing a second emitter complex dissolved in a second solvent on the carrier;

wherein the first emitter complex is not soluble in the second solvent, and the second emitter complex is not soluble in the first solvent; and wherein the first emitter complex and/or the second emitter complex is/are a Cu(I)-complex of the invention.

The method can further comprise the following step:

Depositing a third emitter complex dissolved in a first solvent or in a third solvent on the carrier, wherein the third complex is a Cu(I)-complex of the invention.

In a preferred embodiment, the optoelectronic device is a white-light OLED, wherein the first emitter complex is a red-light emitter, the second emitter complex is a green-light emitter, and the third emitter complex is a blue-light emitter.

FIGURES

FIG. 1: Basic structure of an OLED, not drawn to scale.

Figure 2:
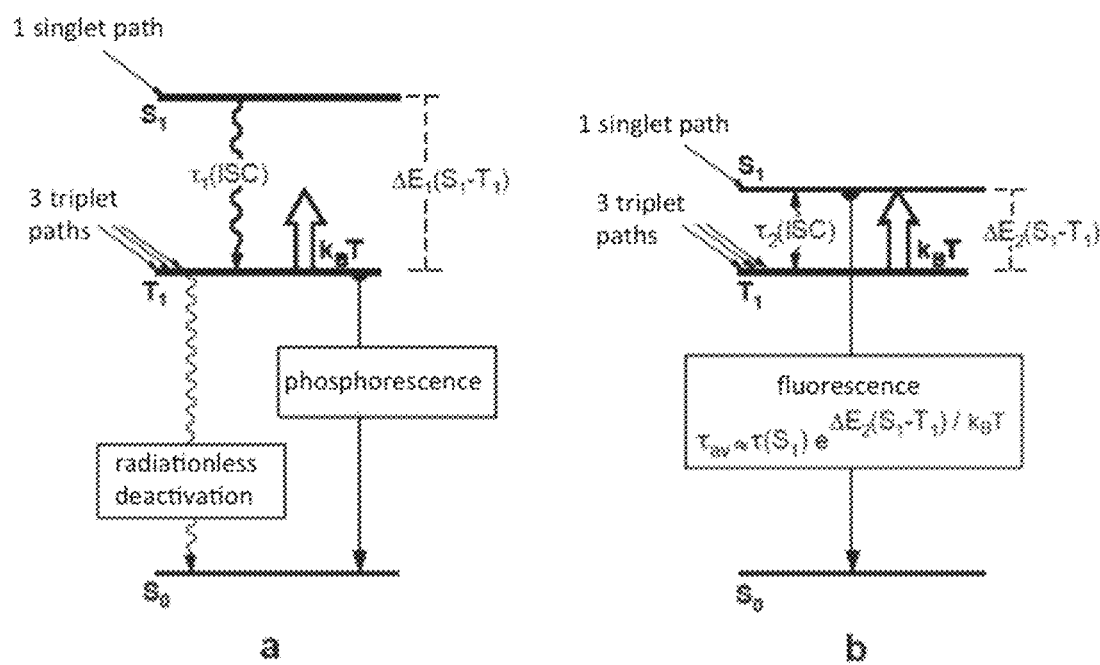

FIG. 2: Illustration of the electro luminescence behavior a for transition metal complexes with a spin orbit coupling that is small or has a small effect (e.g., metal complexes of the first period of the transition metals) and b for Cu(I)-complexes selected according to the present invention. The value of $\tau(T_1)$ in a is an example.

Figure 3:
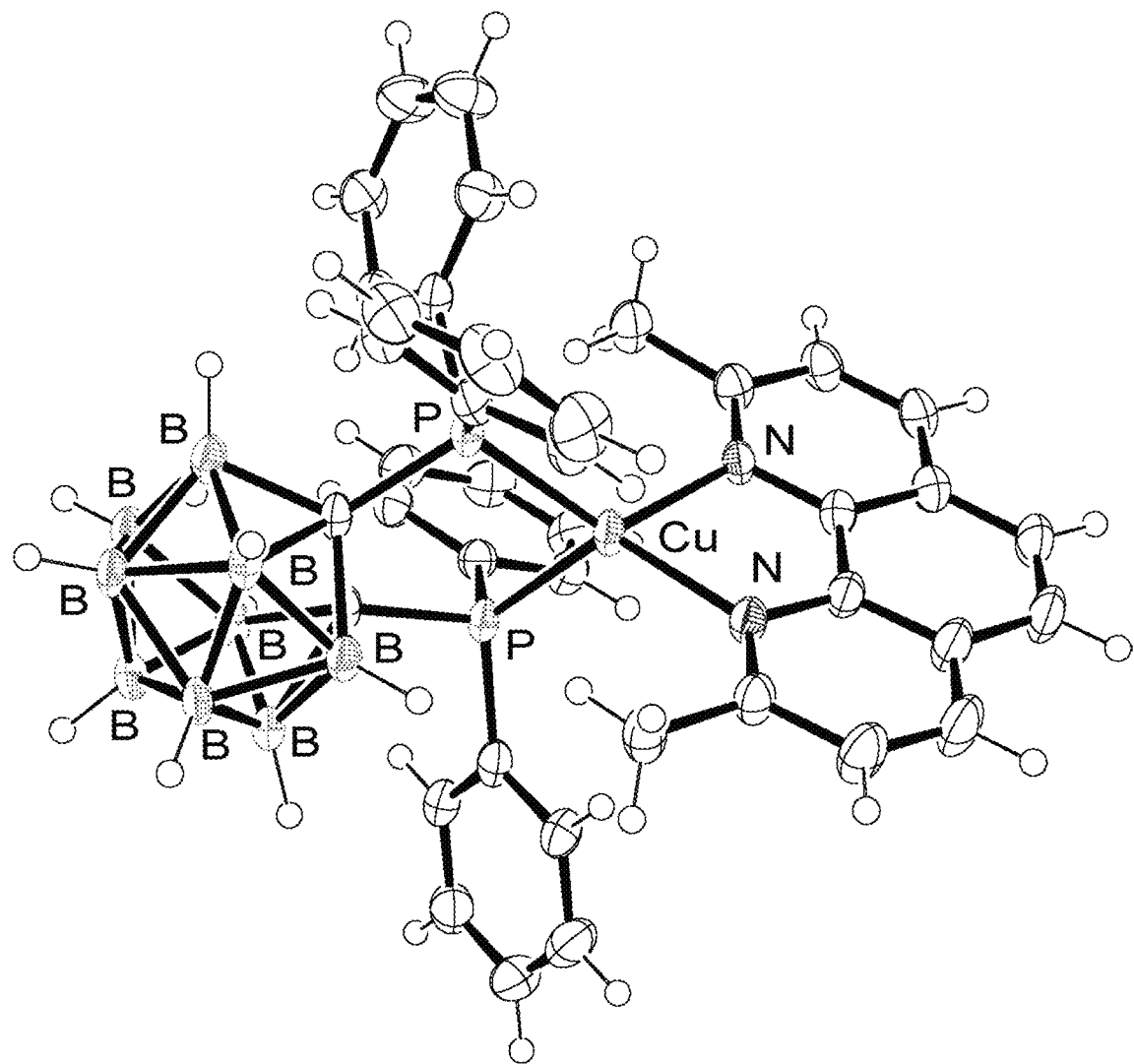

FIG. 3: ORTEP depiction of a Cu(dmphen)(nido-CB (PPh$_2$)$_2$) molecule.

Figure 4:
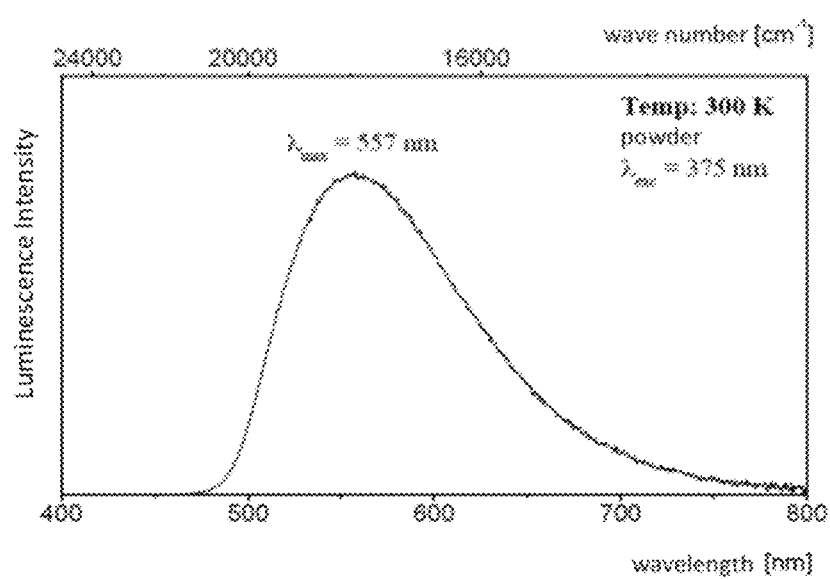

FIG. 4: Photoluminescence spectrum of Cu(dmphen) (nido-CB(PPh$_2$)$_2$) measured with a solid sample at room temperature.

Figure 5:
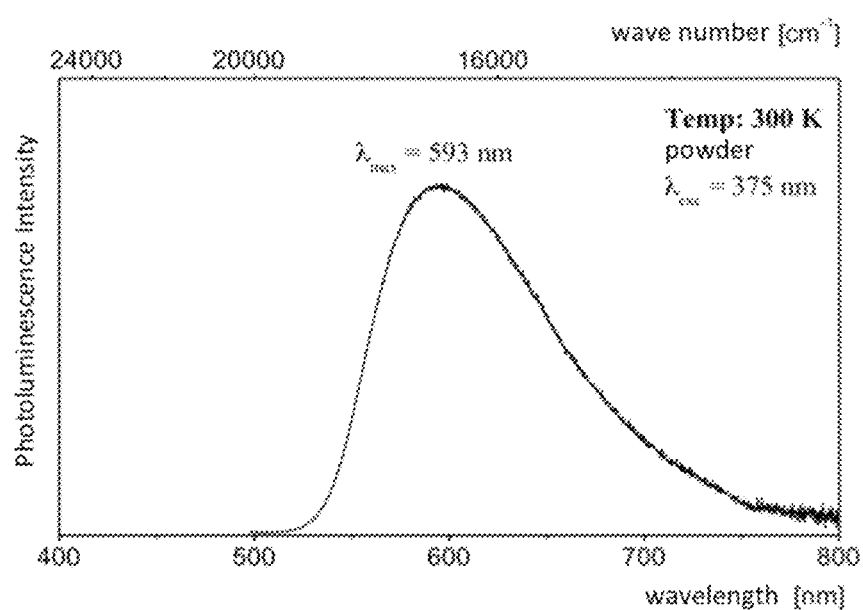

FIG. 5: Photoluminescence spectrum of Cu(dmdpphen) (nido-CB(PPh$_2$)$_2$) measured with a solid sample at room temperature.

Figure 6:
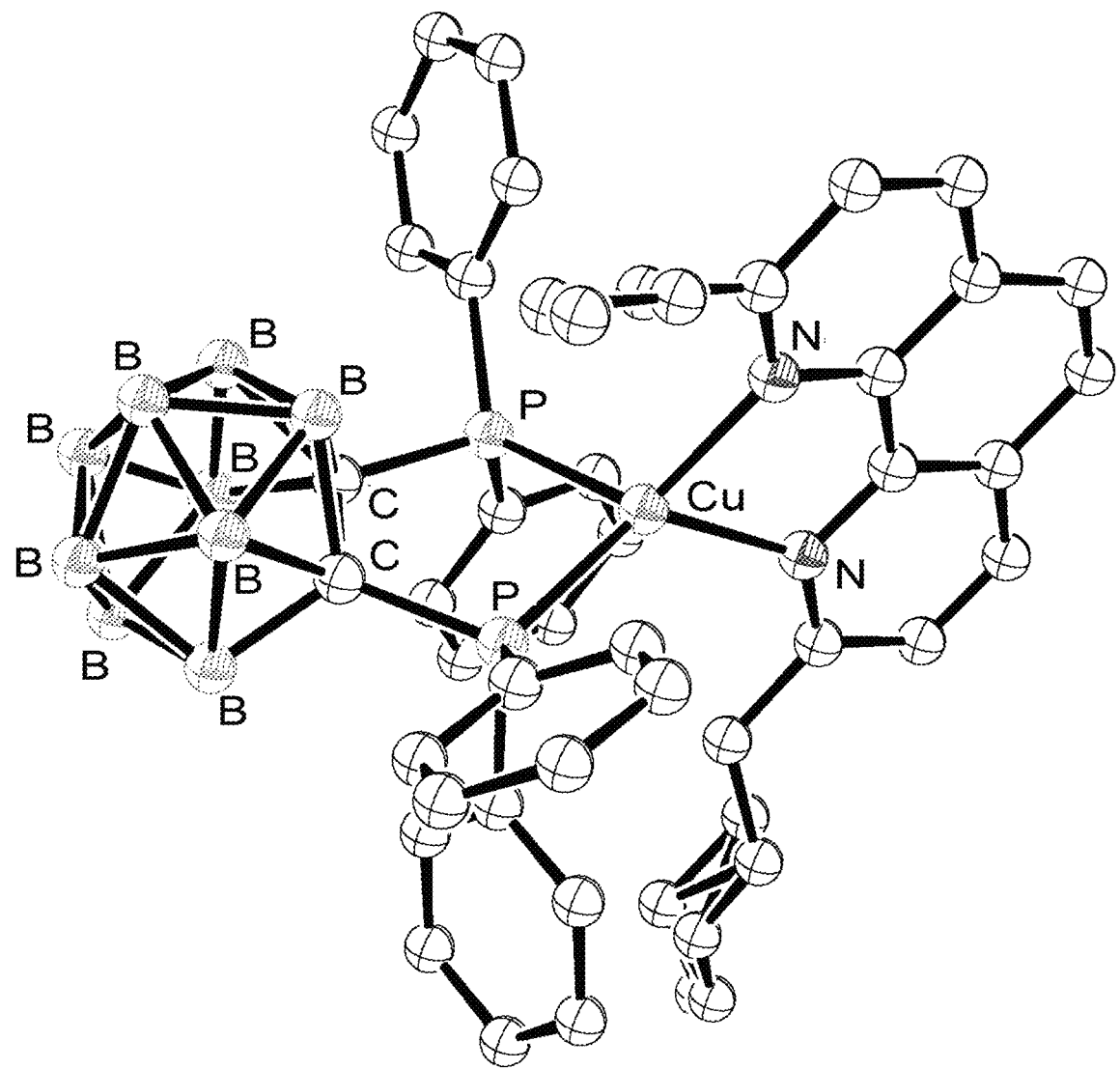

FIG. 6: ORTEP depiction of a Cu(dbphen)(nido-CB (PPh$_2$)$_2$) molecule.

Figure 7:
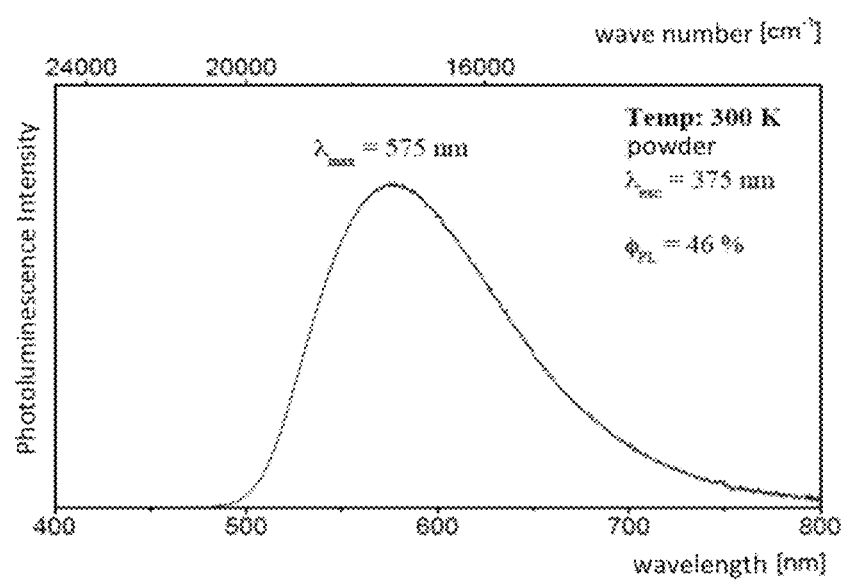

FIG. 7: Photoluminescence spectrum of Cu(dbphen)(nido-CB(PPh$_2$)$_2$) measured with a solid sample at room temperature.

Figure 8:
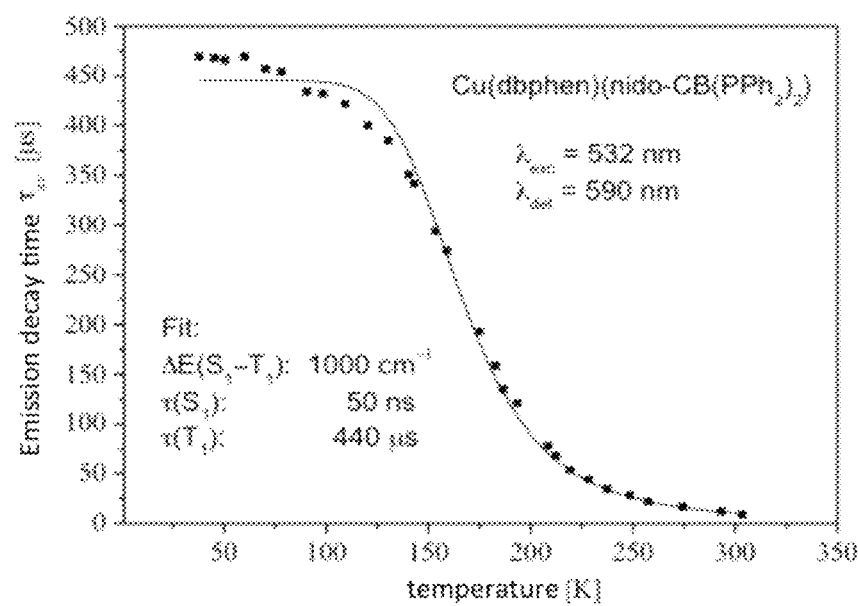

FIG. 8: Temperature dependence of the emission decay time of Cu(dbphen)(nido-CB(PPh$_2$)$_2$) measured with a solid sample at an excitation with 532 nm and detection at 590 nm.

The energy difference $\Delta E(S_1-T_1)$ and the emission decay times of the $S_1$ and $T_1$ states were calculated based on equation (4).

EXAMPLES

Example 1

1,10-Phenanthroline ligands that increase solubility in nonpolar solvents 2,9-dimethyl-4,7-di(n-butyl)-1,10-phenanthroline, Phen2

4,7-dichloro-2,9-dimethyl-1,10-phenanthroline, Phen1, is synthesized according to the literature (M. Schmittel, H. Ammon *Eur. J. Org. Chem.* 1998, 785.). For the substitution with a n-butyl group, an equimolar amount of n-HexMgBr and CuBr is added. The purification of Phen2 is done using column chromatography over silica gel.

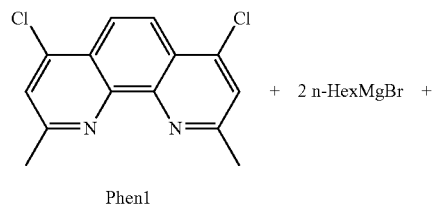

Phen1

+ 2 n-HexMgBr +

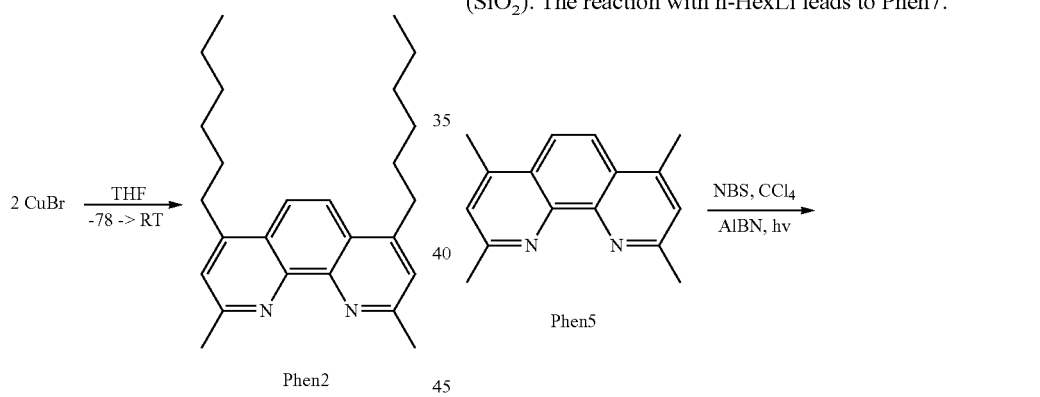

Phen2

Example 2

5,8-di(n-butyl)-1,2,3,4,9,10,11,12-octahydrodibenzo[b,j]-[1,10]phenanthroline, Phen4

The phenanthroline-dichloride Phen3 is synthesized according to (M. Schmittel, H Ammon *Eur. J. Org. Chem.* 1998, 785.). The synthesis of Phen4 is performed analogously to Phen2.

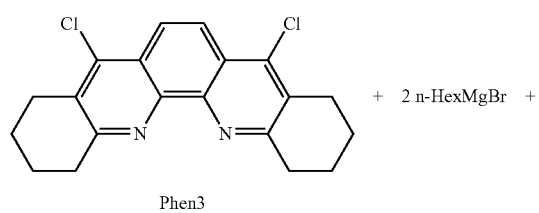

Phen3

+ 2 n-HexMgBr +

2 CuBr $\xrightarrow{\text{THF}}_{-78 \to \text{RT}}$

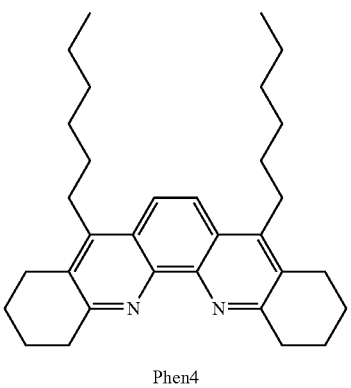

Phen4

Example 3

2,4,7,9-tetra(n-heptyl)-1,10-phenanthroline, Phen7

2,4,7,9-tetra-methyl-1,10-phenanthroline, Phen5, is synthesized according to (G. Butt, R. D. Topsom, *J. Heterocyclic Chem.* 1981, 18, 641). 2,4,7,9-Tetrabromomethylen-1,10-phenanthroline, Phen6, is synthesized via side chain bromation using NBS and isolated by column chromatography (SiO$_2$). The reaction with n-HexLi leads to Phen7.

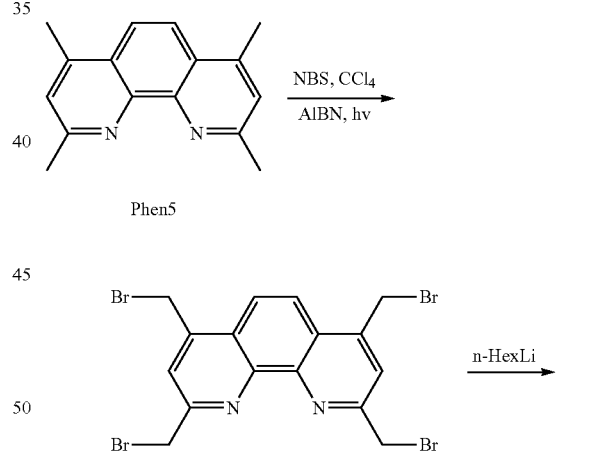

Phen5

Phen6

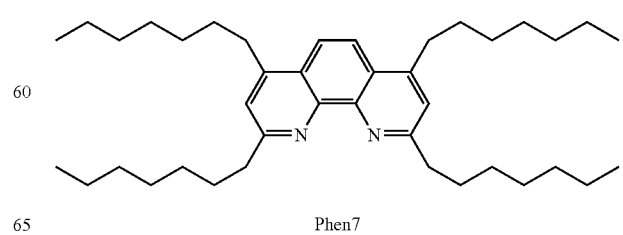

Phen7

Example 4

2,9-dimethyl-4,7-di-(p-hexylphenyl)-1,10-phenanthroline, Phen9

Starting with 4,7-dibromo-2,9-dimethyl-1,10-phenanthroline, Phen8, (M. Schmittel, H. Ammon *Eur. J. Org. Chem.* 1998, 785) and the p-hexylphenylboronic acid (commercially available), the ligand Phen9 is synthesized by a Suzuki-coupling.

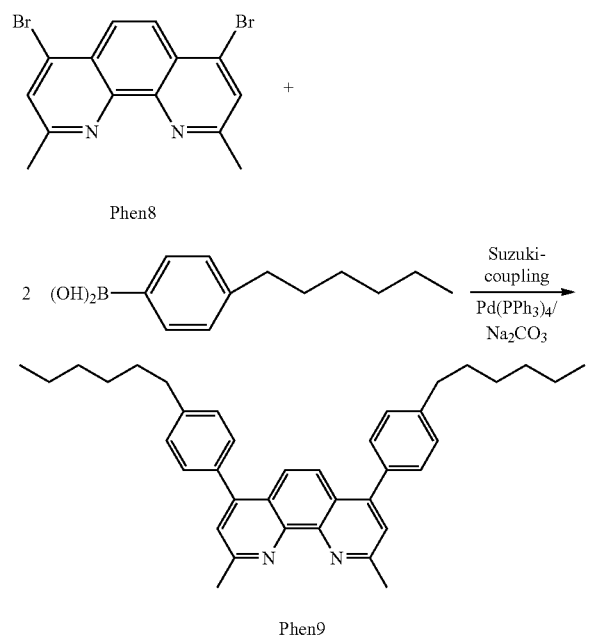

1,10-phenanthroline ligands that increase the solubility in polar solvents, in particular water

Example 5

4,7-bis(methoxy-triethylenglykol)-2,9-dimethyl-[1,10]-phenanthroline-4-ol, Phen10a The diether Phen10a and the monoether Phen10b is synthesized analogously to the literature (B. Koning, J. W. de Boer, A. Meetsma, R. M. Kellogg, *ARKIVOC* 2004, 189). The isolation is performed using column chromatography.

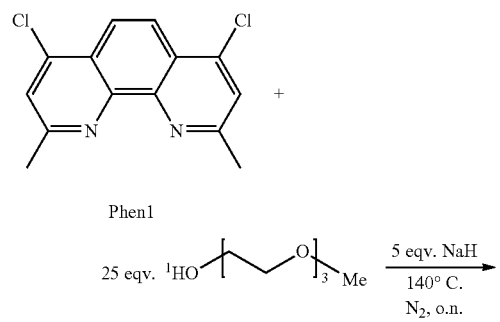

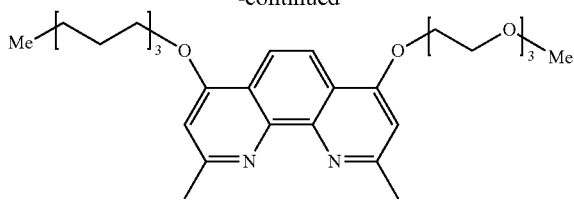

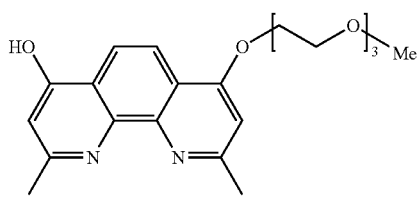

Example 6

4,7-bis(methoxy-polyethylenglykol)-2,9-dimethyl-[1,10]phenanthroline, Phen11a The synthesis of the ligands Phen11a/b is done analogously to Phen10a/b. Used is Methoxy-polyethylenglycol with an average molmass $M_n$=350 g/mol (CAS Nr. 9004-74-4), which is equivalent to n≈8.

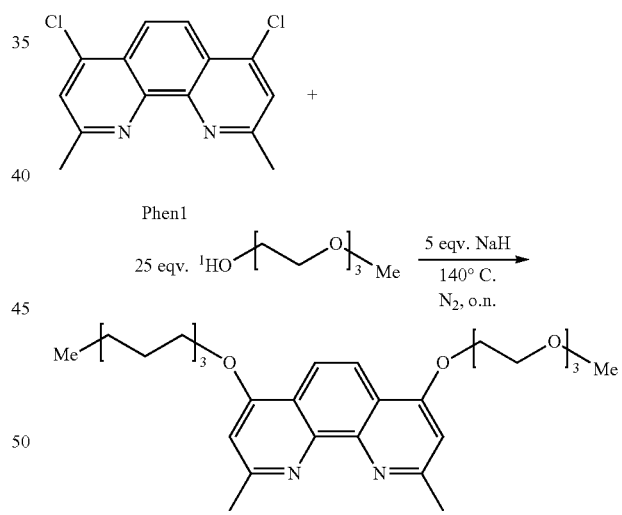

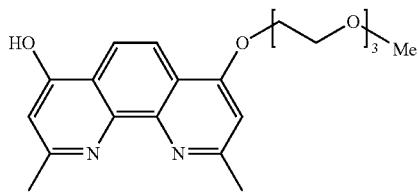

n ≈ 8.

1,10-Phenanthroline ligands that are functionalized with a hole conductor group

Example 7

4,7-bis[(diphenylamino)phenylboronic acid]-2,9-dimethyl-[1,10]phenanthroline, Phen12

Commercially available 4-(Diphenylamino)phenylboronic acid (Aldrich) is coupled with Phen8 to Phen12.

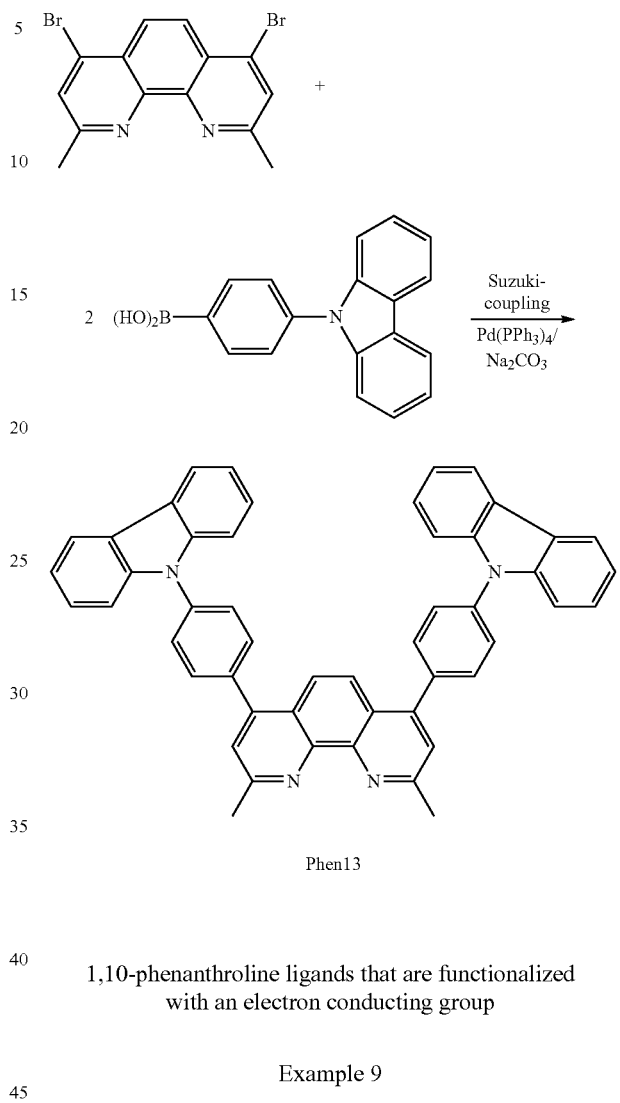

Example 8

4,7-bis[4-(9H-carbozol-9-yl)phenylboronic acid]-2,9-dimethyl-[1,10]phenanthroline, Phen13

Commercially available 4-(9H-carbozol-9-yl)phenylboronic acid is coupled with Phen8 to Phen13.

1,10-phenanthroline ligands that are functionalized with an electron conducting group

Example 9

4,7-bis(1,2,4-triazol)-2,9-dimethyl[1,10]phenanthroline, Phen14

The bromated 1,2,4-triazole is synthesized according to (X. J. Feng, P. L. Wu, H. L. Tam, K. F. Li, M. S. Wong, K. W. Cheah, *Chem.—Eur. J.* 2009, 15, 11681). Through reaction with nBuLi and B(OMe)$_3$ and subsequent hydrolysis with diluted HCl, the boronic acid is synthesized. The boronic acid is reacted analogously to Example 7 to the ligand Phen14.

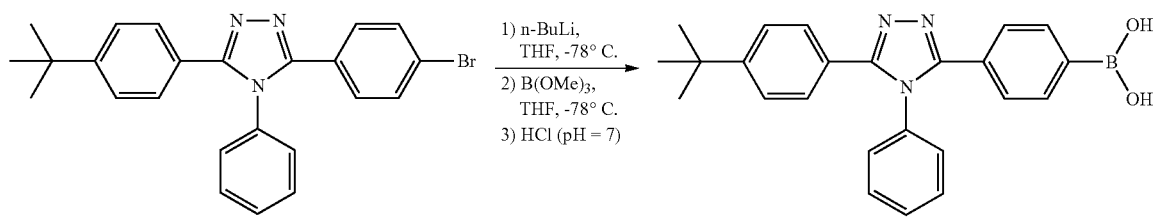

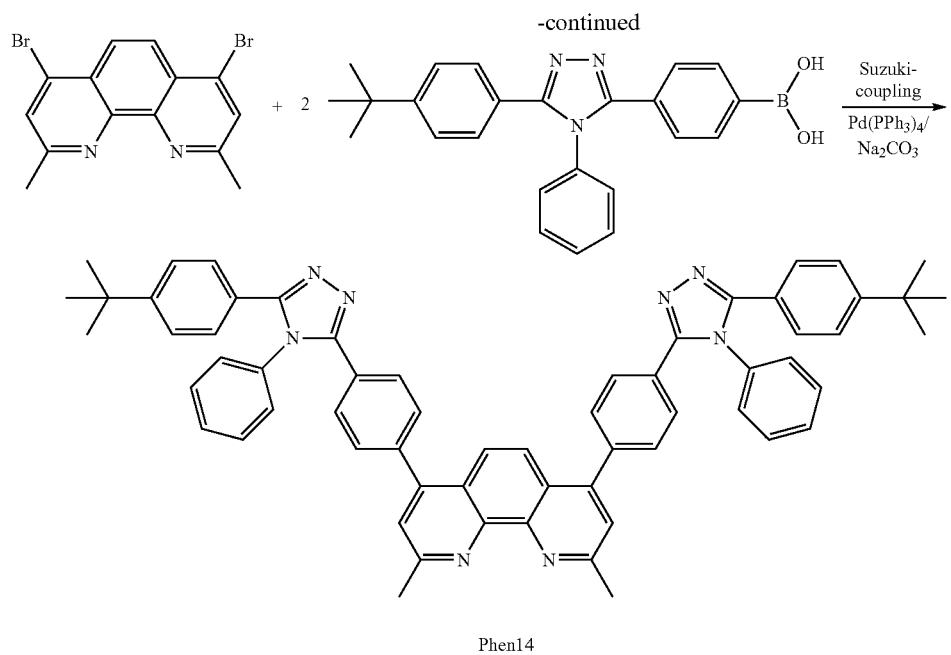

Phen14

1,10-phenanthroline ligands that increase the solubility in organic solvents

Example 10

4,7-bis(hexyloxy)-2,9-dimethyl-1,10-phenanthroline, Phen16

4,7-bis((2-ethylhexyl)oxy)-2,9-dimethyl-1,10-phenanthroline, Phen17

The respective 2,9-dimethyl-1,10-phenanthroline-4,7-diol Phen15 was synthesized according to (A. F. Larsen, T. Ulven, *Org. Lett.* 2011, 13, 3546). By deprotonation with NaH and reaction with the respective Alkyl bromides (H. Frisell, B. Akermark, *Organometallics* 1995, 14, 561), the alkylated ligands Phen16 and Phen17 resulted.

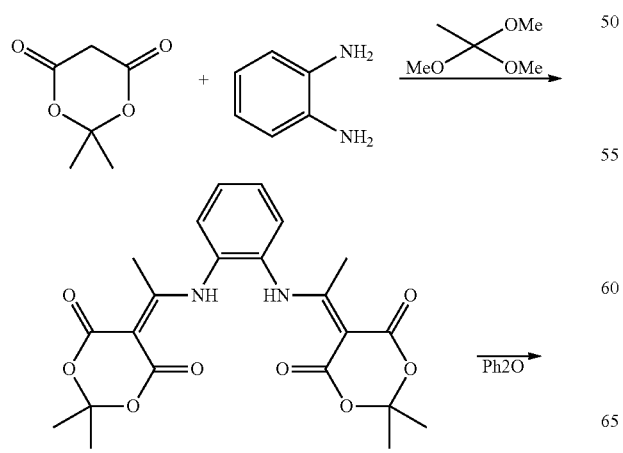

R = Hexyl Phen16
2-Ethylhexyl Phen17

Synthesis of the Singly Negatively Charged L∩L Ligands

Example 11

2-(2-pyridinyl)-1H-indol, (N∩N1)

1-(2-pyridinyl)ethanone was reacted in a Fischer indole synthesis with phenylhydrazine to 2-(2-pyridinyl)-1H-indol according to the literature (R. P. Thummel, V. Hegde, *J. Org. Chem.* 1989, 54 (7), 1720).

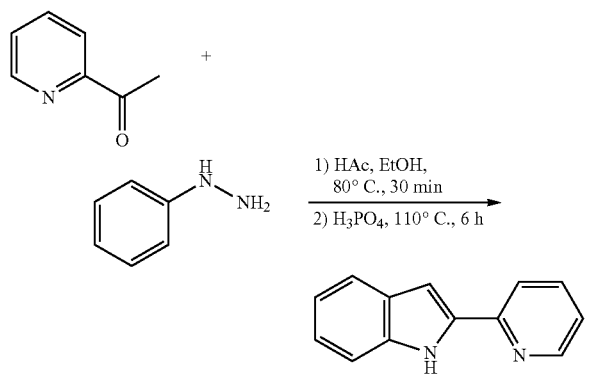

Example 12

Bis(1-pyrazolyl)borate, (N∩N2)

Pyrazole was reacted with NaB(Ph)4 in the molten mass according to the literature (S. Trofimenko, J. Am. Chem. Soc. 1967, 89, 6288) into the corresponding sodium salt of the diphenyldi(1H-1-pyrazolyl)borate, which was converted in a further salt metathesis into the soluble tetrabutyl ammonium-diphenyldi(1H-1-pyrazolyl)borate.

Synthesis of the Cu(I)-Complexes

Using the above-described Phen ligands, the corresponding neutral Cu(Phen)(P∩P) complexes are synthesized with the following, singly negatively charged bisphosphane:

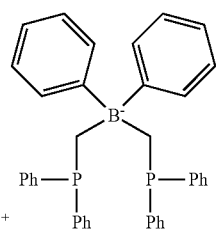

[n-Bu$_4$N](P∩P) is synthesized according to (J. C. Peters, J. C. Thomas, Inorg. Synth. 2004, 34, 11).

Under nitrogen atmosphere, equimolar amounts of [n-Bu$_4$N](P∩N) and [Cu(CH$_3$CN)$_4$]PF$_6$ are stirred into acetonitrile. After 2 h, the corresponding Phen ligand is added. The product precipitates and is filtered out. After washing with water, cold acetonitrile and diethyl ether, the product is dried under vacuum.

In this manner, the following complexes are synthesized:

Example 13

Cu(Phen2)(P∩P)

Example 14

Cu(Phen4)(P∩P)

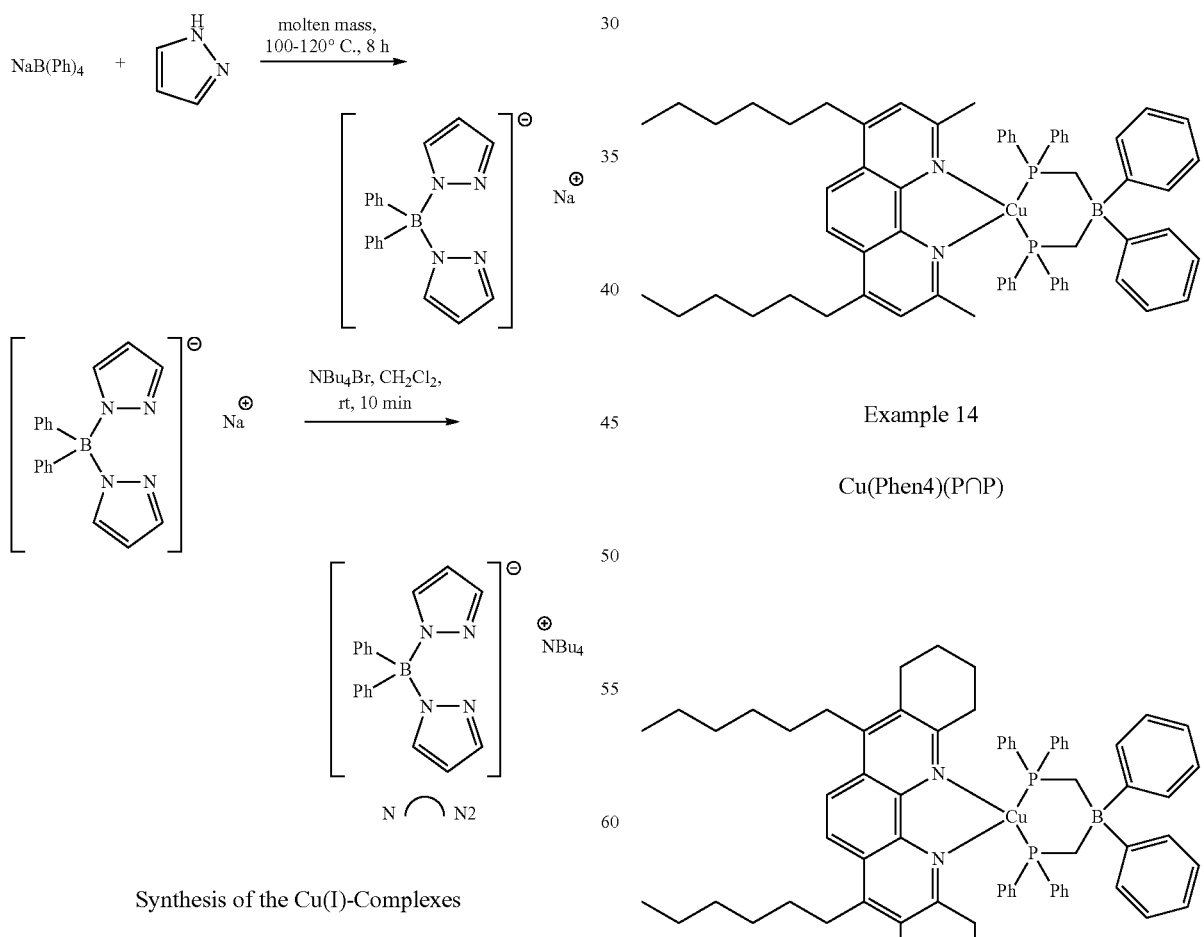

Example 15
Cu(Phen7)(P∩P)
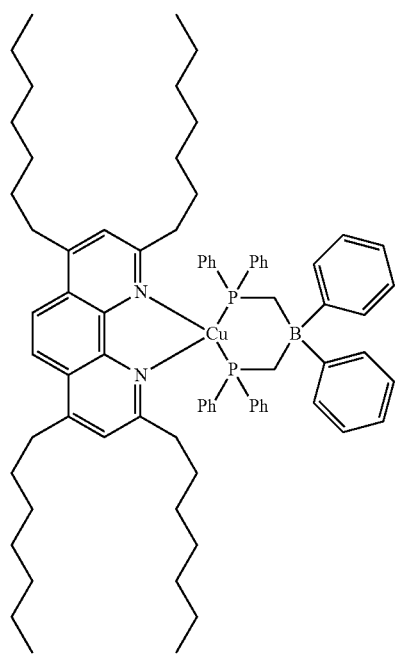
Example 16
Cu(Phen9)(P∩P)
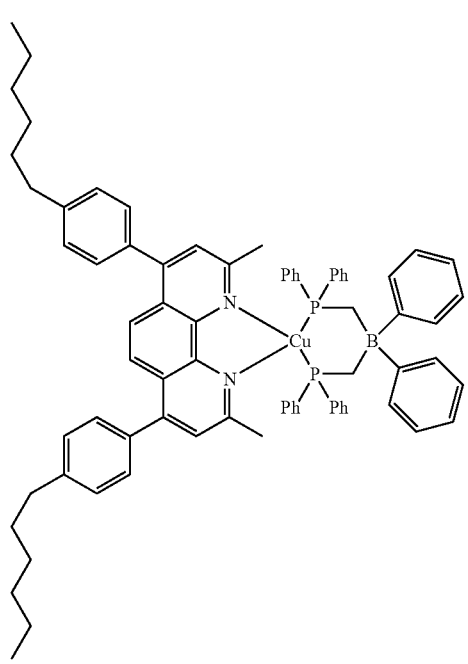
Example 17
Cu(Phen10a)(P∩P)
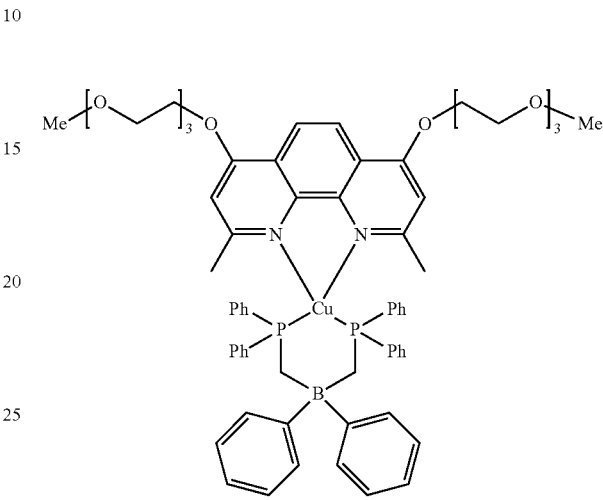
Example 18
Cu(Phen11a)(P∩P)
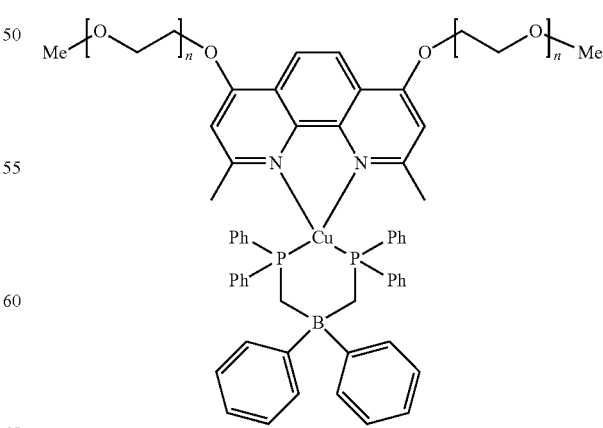
n ≈ 8.

39
Example 19
Cu(Phen12)(P∩P)
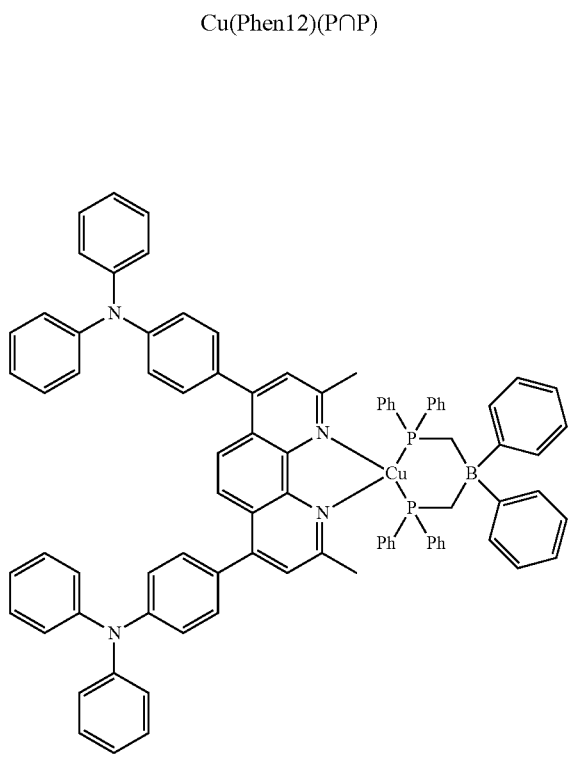
Example 20
Cu(Phen13)(P∩P)
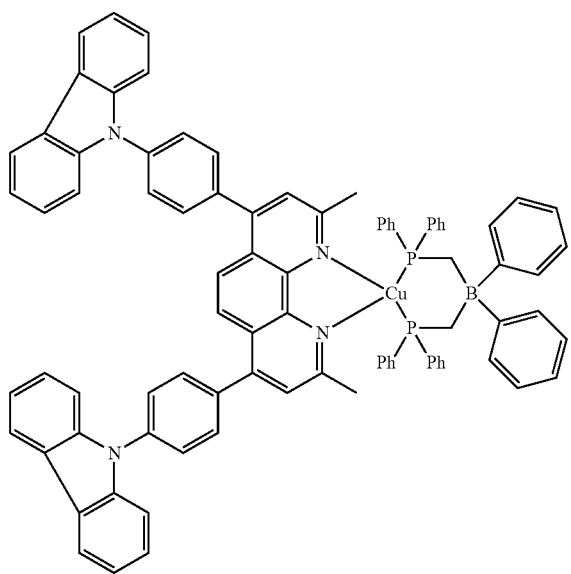
40
Example 21
Cu(Phen14)(P∩P)
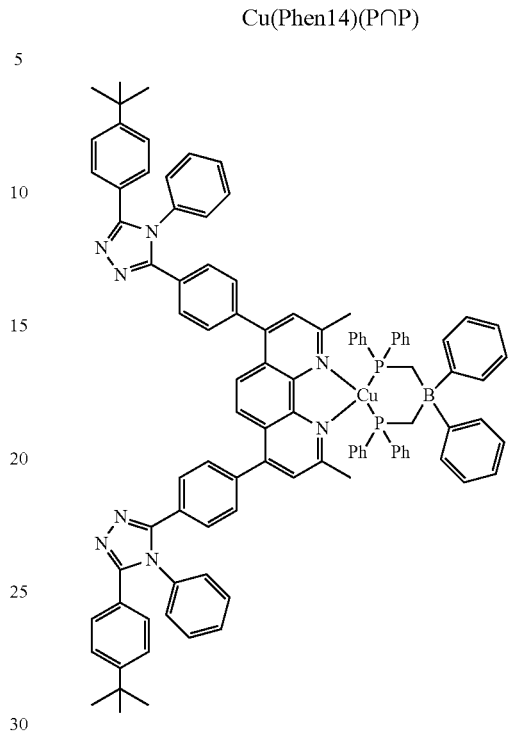
Example 22
Cu(Phen16)(P∩P)
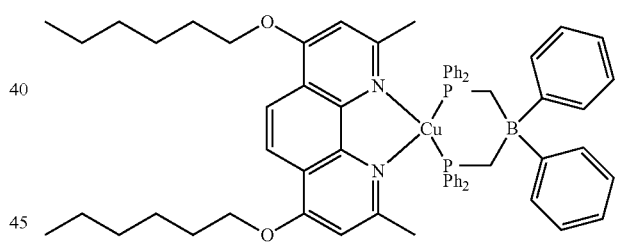
Example 23
Cu(Phen17)(P∩P)
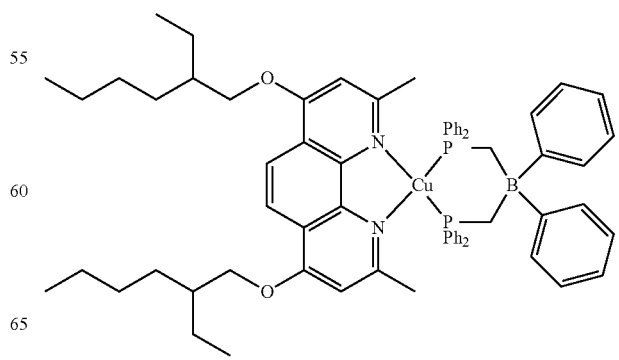

Example 24

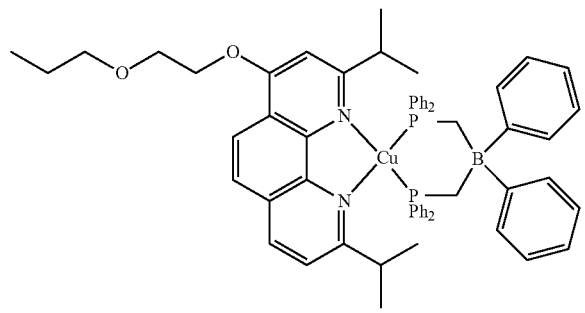

Example 25

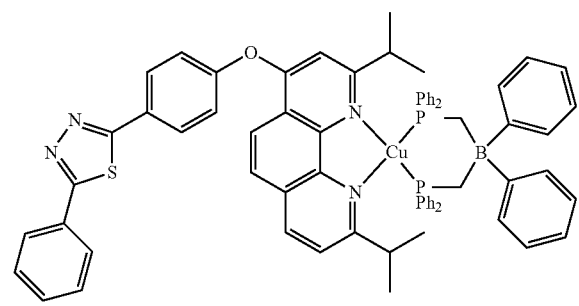

Example 26

Cu(dmphen)(nido-CB(PPh$_2$)$_2$) (CB=C$_2$B$_9$H$_{10}$)

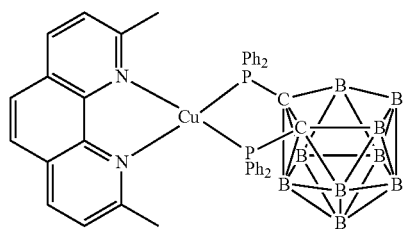

Synthesis Pathway

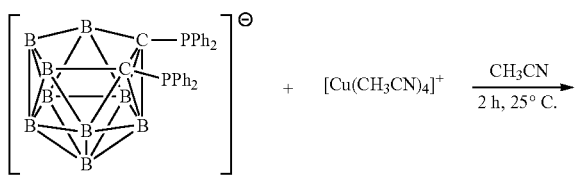

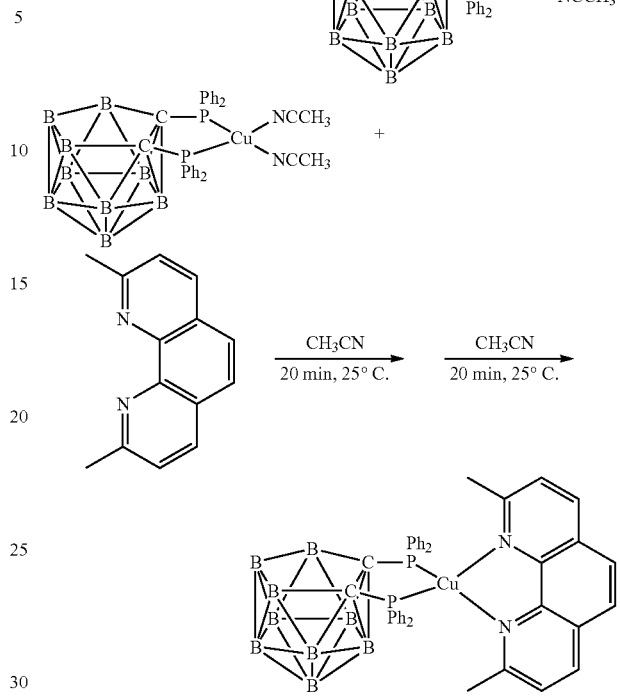

A solution of 330 mg (0.44 mmol) tetrapropylammonium 7,8-bis-(diphenylphosphino)-7,8-dicarba-nido-undecarborate (NPr$_4$$^+$ nido-CB(PPh$_2$)$_2$$^-$, (synthesized according to Zakharkin, L. I.; Kalinin, V. N. *Tetrahedron Lett.* 1965, 7, 407.) and 163 mg (0.44 mmol) Cu(CH$_3$CN)$_4$$^+$PF$_6$$^-$ in 50 ml acetonitrile were stirred under nitrogen for 2 h at 25° C. Subsequently, 91 mg (0.44 mmol) neocuproine (dmphen) were added. The product Cu(dmphen)(nido-CB(PPh$_2$)$_2$) precipitates as a yellow powder and is filtered out. The raw product is washed with water, cold acetonitrile, and diethylether and dried under vacuum.

Yield: 300 mg (88%).

Elementary analysis: C, 61.23%; H, 5.36%; N, 3.52%.

For C$_{40}$H$_{42}$N$_2$B$_9$CuP$_2$ expected: C, 62.11%; H, 5.47%; N, 3.62%.

ES-MS: e/z=773.4 (M$^+$)

Crystallization from a dichloromethan/toluol mixture resulted in crystals of Cu(dmphen)(nido-CB(PPh$_2$)$_2$)×CH$_2$Cl$_2$ suitable for X-ray structure analysis. In FIG. 3, an ORTEP depiction of a Cu(dmphen)(nido-CB(PPh$_2$)$_2$) molecule is shown. Its luminescence characteristics, measured using a solid sample at room temperature, are shown in FIG. 3.

TABLE 1

Photoluminescence data for Cu(dmphen)(nido-CB(PPh$_2$)$_2$) (measured under nitrogen protective atmosphere)

| Conditions: | solid (300 K) | PMMA (300 K) | PMMA (77 K) |
| --- | --- | --- | --- |
| Emission maximum: | 557 nm | 577 nm | 597 nm |
| Emission decay time τ: | 11 μs | 14 μs | 600 μs |
| Quantum yield φ$_{PL}$: | 55 % | 40 % | |

The pronounced decrease of the emission decay time with increase in temperature form T=77 K (600 μs) to 300 K (14

μs) by a factor of greater 40—at the measured $\phi_{PL}$-value of 40%—is proof for the thermic population of a shorter-lived emitting electronic state, i.e. is proof for the occurrence of the singlet harvesting effect.

Example 27

Cu(dmdpphen)(nido-CB(PPh$_2$)$_2$) (CB=C$_2$B$_9$H$_{10}$)

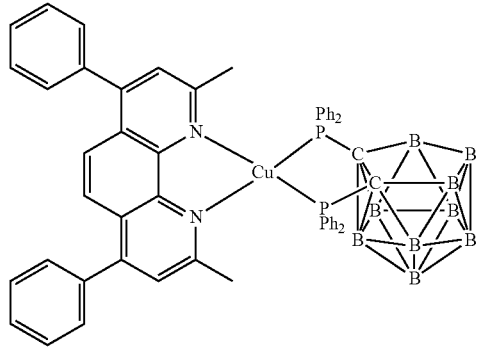

Synthesis Pathway

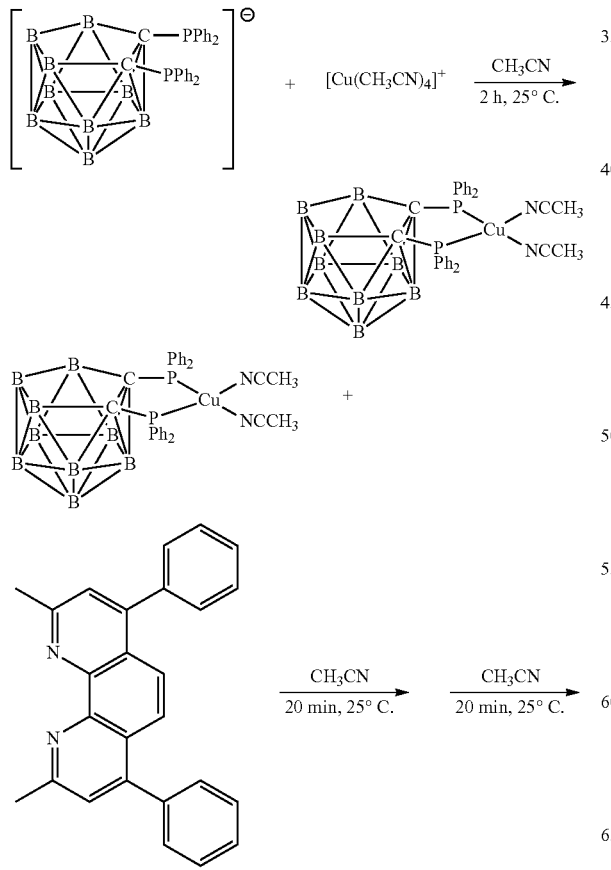

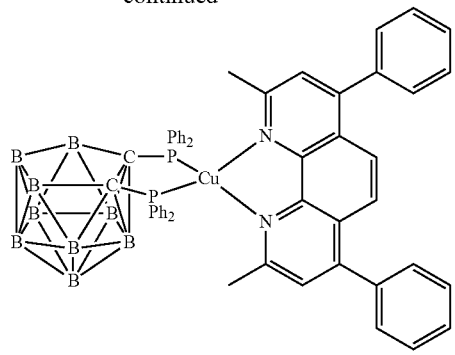

A solution of 188 mg (0.25 mmol) tetrapropylammonium-7,8-bis-(diphenylphosphino)-7,8-dicarba-nido-undecarborate (NPr$_4^+$ nido-CB(PPh$_2$)$_2^-$) and 93 mg (0.25 mmol) Cu(CH$_3$CN)$_4^+$PF$_6^-$ in 50 ml acetonitrile were stirred under nitrogen for 2 h at 25° C. Subsequently, 90 mg (0.25 mmol) bathocuproine (dmdpphen) were added. The product Cu(dmdpphen)(nido-CB(PPh$_2$)$_2$) precipitates as a yellow powder and is filtered out. The raw product is washed with water, cold acetonirile, and diethylether and dried under vacuum.

Yield: 200 mg (86%).

The luminescence characteristics of Cu(dmdpphen)(nido-CB(PPh$_2$)$_2$), measured with a solid sample at room temperature are shown in FIG. 5.

Example 28

Cu(dbphen)(nido-CB(PPh$_2$)$_2$) (CB=C$_2$B$_9$H$_{10}$)

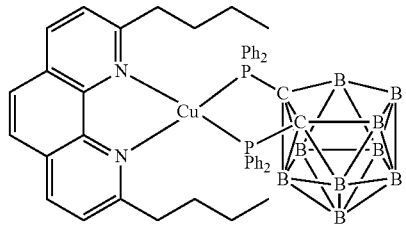

Synthesis Pathway

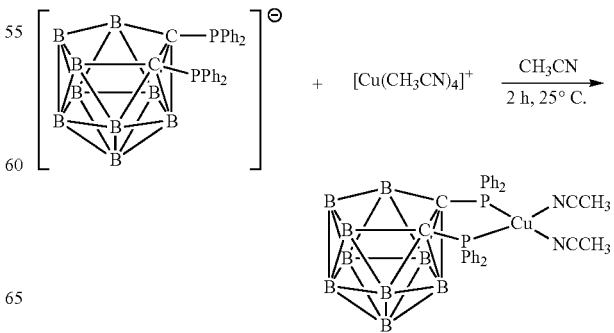

-continued

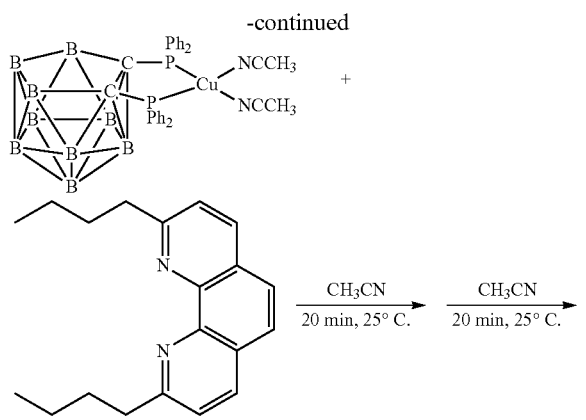

A solution of 150 mg (0.2 mmol) tetrapropylammonium-7,8-bis-(diphenylphosphino)-7,8-dicarba-nido-undecaborate (NPr$_4^+$ nido-CB(PPh$_2$)$_2^-$) and 74 mg (0.2 mmol) Cu(CH$_3$CN)$_4^+$PF$_6^-$ in 50 ml acetonitrile was stirred under nitrogen for 2 h at 25° C. Subsequently, 58 mg (0.2 mmol) 2,9-di-n-butylphenanthroline (dbphen) were added. The product Cu(dmphen)(nido-CB(PPh$_2$)$_2$) precipitates as a yellow powder and is filtered out. The raw product is washed with water, cold acetonitrile, and diethylether and dried under vacuum.

Yield: 145 mg (85%).

Elementary analysis: C, 63.51%; H, 6.12; N, 3.14%.

For C$_{46}$H$_{54}$N$_2$B$_9$CuP$_2$ expected: C, 64.41%; H, 6.35%; N, 3.27%.

ES-MS: e/z=858.5 (M$^+$)

Cu(dbphen)(nido-CB(PPh$_2$)$_2$) is crystallized from a mixture of dichlormethan and toluol. In FIG. 6, an ORTEP depiction of a Cu(dbphen)(nido-CB(PPh$_2$)$_2$) molecule is shown.

A photoluminescence spectrum of Cu(dbphen)(nido-CB(PPh$_2$)$_2$), measured with an solid sample at room temperature, is shown in FIG. 7.

TABLE 2

Photoluminescence data for Cu(dbphen)(nido-CB(PPh$_2$)$_2$) (measured under nitrogen protective atmosphere)

| Conditions: | solid (300 K) | PMMA (300 K) | PMMA (77 K) |
|---|---|---|---|
| Emission maximum: | 575 nm | 575 nm | 579 nm |
| Emission decay time τ: | 5 μs | 11 μs | 700 μs |

The pronounced decrease of the emission decay time with increase in temperature form T=77 K (700 μs) to 300 K (11 μs) by a factor of greater 60—at the measured high quantum yields—is proof for the thermic population of a shorter-lived emitting electronic state, i.e. is proof for the occurrence of the singlet harvesting effect.

FIG. 8 shows the dependence of the emissions decay time as a function of the temperature measured for a Cu(dbphen)(nido-CB(PPh$_2$)$_2$) solid sample. About below T=100 K, a plateau is visible that represents the emission decay time of the T$_1$ state of ca. 440 μs. The drawn curve represents a fit-function according to equation (4). The resulting fir-values for τ(S$_1$) and ΔE(S$_1$–T$_1$) are given in FIG. 8.

Further Examples

Example 29

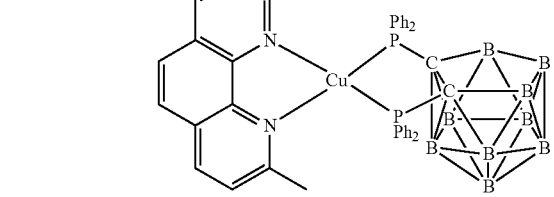

Example 30

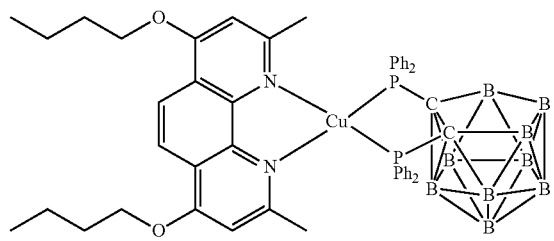

Example 31

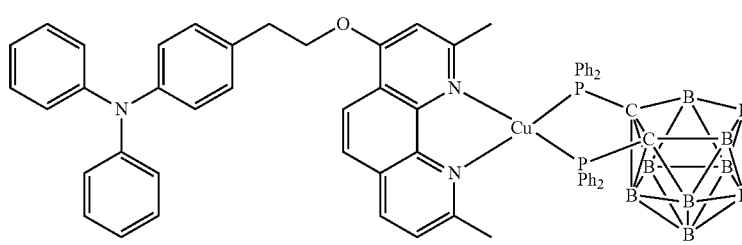

Example 32

Using the above-described Phen ligands and the singly negatively charged L∩L ligands, the corresponding neutral Cu(Phen)(L∩L) complexes were synthesized:

Under nitrogen protective atmosphere, 2-(2-pyridinyl)indole, N∩N1 was deprotonated in THF with nBuLi at room temperature, stirred for 1 hour and the equimolar amount of [Cu(CH$_3$CN)$_4$]PF$_6$ was added. After 2 h, the corresponding Phen ligand was added. The product precipitated and was filtered out. After washing with water, cold acetonitrile and diethyl ether, the product was dried under vacuum.

Cu(Phen16)(N∩N1)

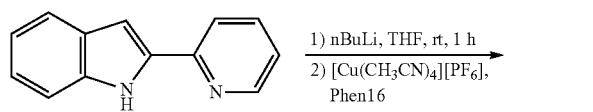

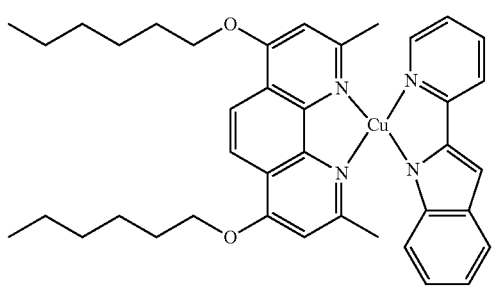

Example 32

Cu(Phen17)(N∩N1)

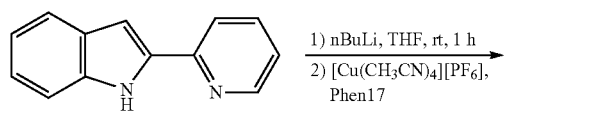

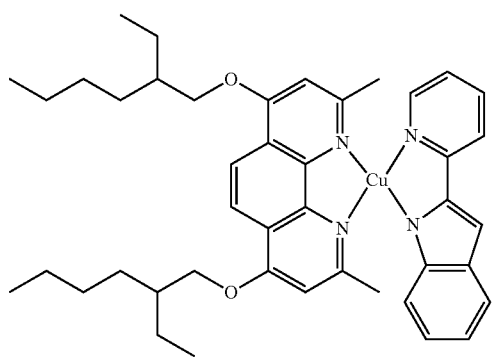

Example 33

Cu(BCP)(N∩N1)

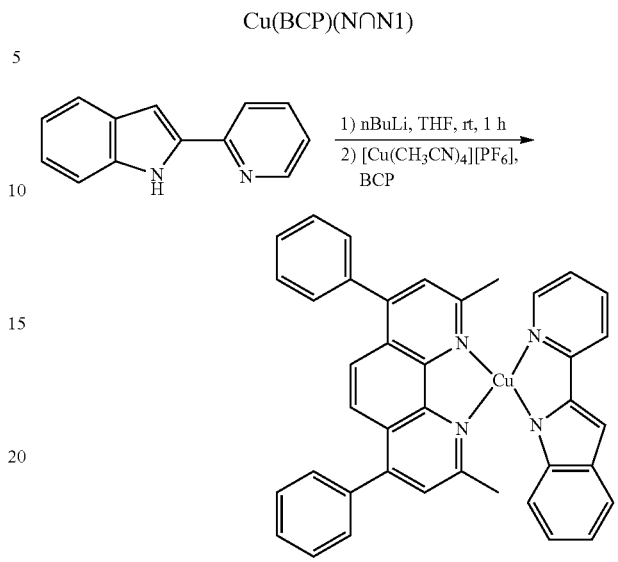

Example 34

Cu(Phen17)(N∩N)

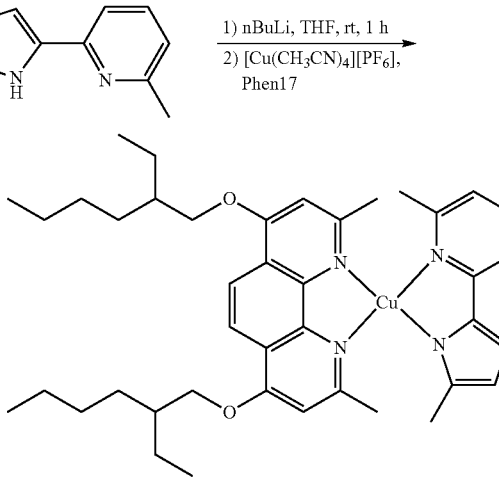

Example 35

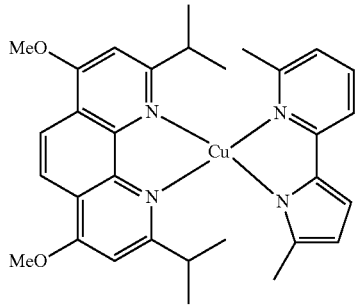

Example 36

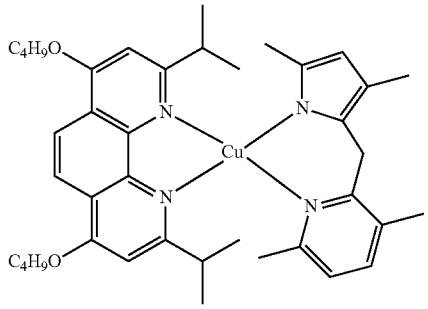

Example 37

Under nitrogen atmosphere, 8-Quinolinol was deprotonated in THF with nBuLi at room temperature, stirred for 1 hour and the equimolar amount of [Cu(CH$_3$CN)$_4$]PF$_6$ was added. After 2 h, the corresponding Phen ligand was added in an equimolar amount. The product precipitated and was filtered out. After washing with water, cold acetonitrile and diethyl ether, the product was dried under vacuum.

Cu(Phen16)(N∩O)

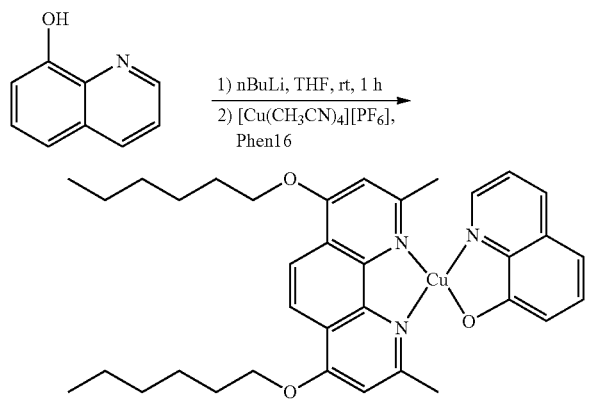

Example 38

Cu(Phen17)(N∩O)

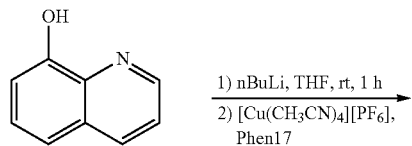

Example 39

Cu(BCP)(N∩O)

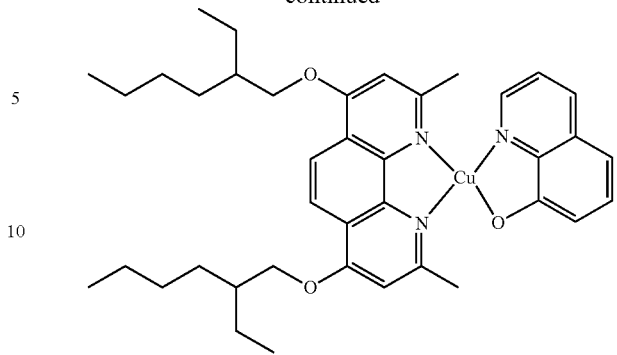

Example 40

Under nitrogen atmosphere, equimolar amounts of [n-Bu$_4$N](N∩N2) and [Cu(CH$_3$CN)$_4$]PF$_6$ were stirred in acetonitrile. After 2 h, the corresponding Phen ligand was added in equimolar amounts. The product precipitated and was filtered out. After washing with water, cold acetonitrile and diethyl ether, the product was dried under vacuum.

Cu(Phen16)(N∩N2)

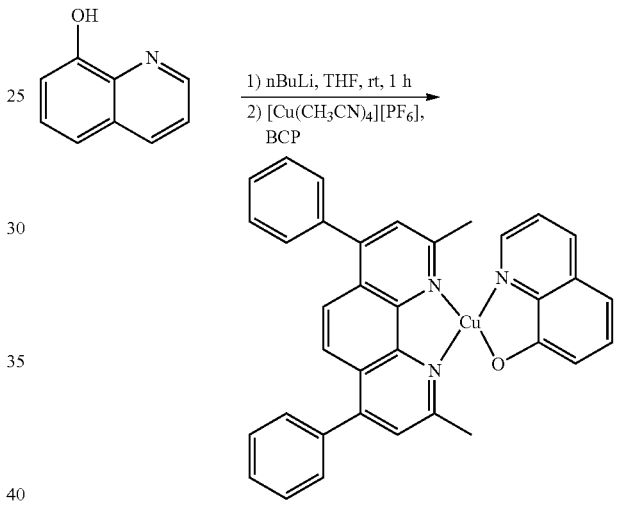

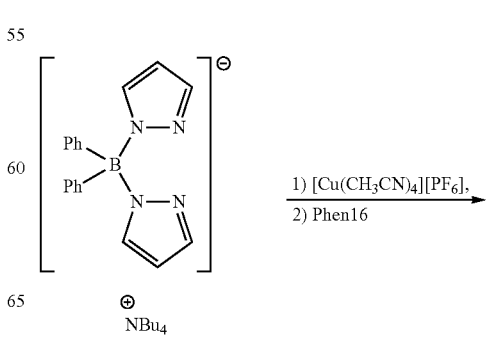

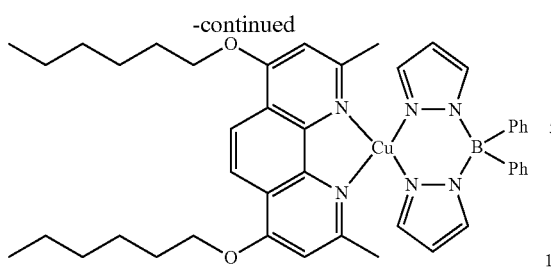

Example 41

Cu(Phen17)(N∩N2)

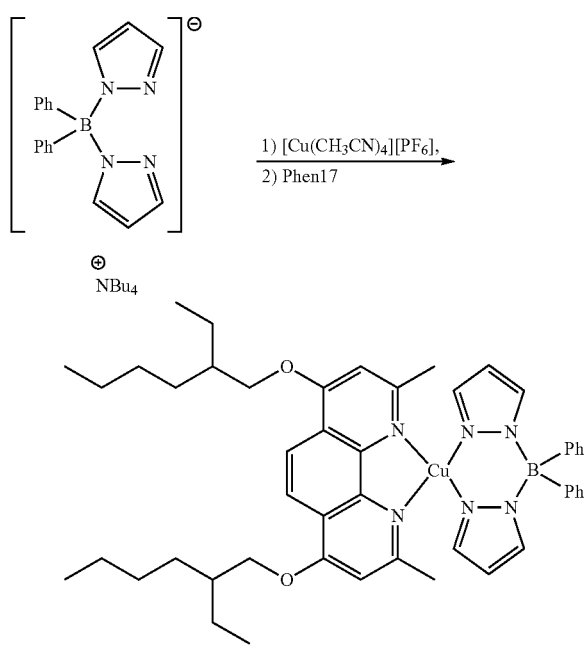

The invention claimed is:

1. A neutral mononuclear copper(I) complex for the emission of light with a structure according to formula A Formula A

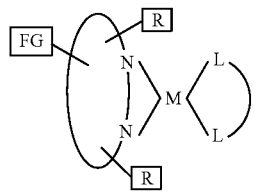

wherein:
M is Cu(I);
L∩L is a single negatively charged bidentate ligand, wherein the single negatively charged bidentate ligand is a substituted 2,2'-bipyridine-derivative (bpy) or a 1,10-phenanthroline-derivative (phen);
N∩N is a diimine ligand, substituted with R and FG;
R are substituents in 3,3'-position (bpy) or 2,9-position (phen) for preventing a change of geometry of copper(I) complexes towards a planarization in an excited state;
function group FG is at least one substituent for conducting electrons and for increasing the solubility in organic solvents, or at least one substituent for conducting holes and for increasing the solubility in organic solvents,
wherein FG is bound either directly or via a bridge to the diimine ligand,
wherein the copper(I) complex has:
a $\Delta E(S_1-T_1)$-value between the lowest excited singlet ($S_1$)-state and the triplet ($T_1$)-state below of less than 2500 $cm^{-1}$;
an emission decay time of at most 20 μs;
an emission quantum yield larger than 40%, and
a solubility in organic solvents of at least 1 g/L.

2. The copper(I) complex of claim 1, wherein:
the bpy-ligand is substituted at the 3,3'-position with a branched or unbranched alkyl substituent [$CH_3$—$(CH_2)_n$—] (n=1-20) or an aryl substituent, or
the phen-ligand is substituted at the 2,9-position with a branched or unbranched alkyl substituent [$CH_3$—$(CH_2)_n$—] (n=1-20) or an aryl substituent.

3. The copper(I) complex of claim 1, wherein the at least one sterically demanding substituent R for preventing the planarization of the complex in the excited state is selected from the group consisting of branched or unbranched alkyl groups —$(CH_2)_n$—$CH_3$ (n=0-20), aryl groups comprising 6-20 carbon atoms, alkoxy groups —O—$(CH_2)_n$—$CH_3$ (n=0-20), aryloxy groups and silane groups.

4. The copper(I) complex of claim 3 wherein the alkyl or aryl groups are substituted and/or are fused to form anellated ring systems.

5. The copper(I) complex of claim 1, wherein the at least one sterically demanding substituent R increases the solubility of the copper(I) complexes in organic solvents and/or increases the hole or electron conductivity.

6. The copper(I) complex of claim 1, wherein the at least one sterically demanding substituent R for preventing the planarization of the complex at the excited state is:
an aliphatic group.

7. The copper(I) complex of claim 1, wherein the copper(I) complex has:
a $\Delta E(S_1-T_1)$-value of less than 1500 $cm^{-1}$,
an emission quantum yield of larger than 40%,
an emission life time of at the most 10 μs, and/or
a solubility in organic solvents of at least 10 g/L.

8. A method for emitting light comprising the steps of:
providing an optoelectronic device; and
using the copper(I) complex of claim 1 in the optoelectronic device,
whereby light is emitted from the optoelectronic device.

9. The method of claim 8 wherein the copper(I) complex is in an emitter layer in the optoelectronic device.

10. The method of claim 9, wherein the optoelectronic device is selected from the group consisting of organic light-emitting diodes (OLEDs), light-emitting electrochemical cells (LEECs or LECs), OLED-sensors, optical temperature sensors, organic solar cells (OSCs), organic field-effect transistors, organic lasers, organic diodes, organic photo diodes and down conversion systems.

11. A method for manufacturing an optoelectronic device, comprising the steps of:
providing the copper(I) complex of claim 1; and
using the copper(I) complex in the optoelectronic device.

12. The method of claim 11, wherein the manufacturing is performed wet-chemically, the method comprising the steps of:
depositing a first emitter complex onto a carrier, wherein the first emitter complex is dissolved in a first solvent, and
depositing a second emitter complex onto the carrier, wherein the second emitter complex is dissolved in a second solvent,
wherein:
the first emitter complex is not soluble in the second solvent,
the second emitter complex is not soluble in the first solvent, and
the first emitter complex and/or the second emitter complex is a copper(I) complex of claim 1.

13. The method of claim 12, the method comprising the step of depositing a third emitter complex onto the carrier, wherein the third emitter complex:
is dissolved in the first solvent or in the third solvent, and
is a copper(I) complex of claim 1.

14. The method of claim 13, wherein the optoelectronic device is a white light-OLED, wherein:
the first emitter complex is a red light emitter,
the second emitter complex is a green light emitter, and
the third emitter complex is a blue light emitter.

15. The method of claim 13, wherein the optoelectronic device is selected from the group consisting of organic light-emitting diodes (OLEDs), light-emitting electrochemical cells (LEECs or LECs), OLED-sensors, optical temperature sensors, organic solar cells (OSCs), organic field-effect transistors, organic lasers, organic diodes, organic photo diodes and down conversion systems.

16. An optoelectronic device comprising:
a copper(I) complex of claim 1.

17. The optoelectronic device of claim 16, wherein the fraction of the copper(I) complex in the emitter layer is 2 to 100 weight-%, with respect to the total weight of the emitter layer.

18. The optoelectronic device of claim 16 in the form of an organic light-emitting diode (OLED), comprising:
an emitter layer that comprises the copper(I) complex, wherein the fraction of the copper(I) complex in the emitter layer is between 2 to 100 weight-%, with respect to the total weight of the emitter layer.

19. The optoelectronic device of claim 16, wherein the optoelectronic device is selected from the group consisting of organic light-emitting diodes (OLEDs), light-emitting electrochemical cells (LEECs or LECs), OLED-sensors, optical temperature sensors, organic solar cells (OSCs), organic field-effect transistors, organic lasers, organic diodes, organic photo diodes and down conversion systems.

20. A method for selecting a copper(I) complex of claim 1, wherein the copper(I) complex has an $\Delta E(S_1-T_1)$-value between the lower most excited singlet state ($S_1$) and the triplet state ($T_1$) below $S_1$ of less than 2500 cm$^{-1}$, the method comprising the steps of:
determining the $\Delta E(S_1-T_1)$-value, the determining step comprising the step of:
calculating an up-initio molecular calculation,
measuring the temperature dependence of the fluorescence intensity and/or phosphorescence intensity, or
measuring the temperature dependence of the emission decay time; and
determining the organic molecule whose $\Delta E(S_1-T_1)$-value is less than 2500 cm$^{-1}$.

21. The copper(I) complex of claim 1, wherein R is FG, provided that R is a substituent that conducts electrons, conducts holes, or increases solubility.

* * * * *